(12) United States Patent
Lau et al.

(10) Patent No.: US 7,435,213 B2
(45) Date of Patent: *Oct. 14, 2008

(54) DEVICE FOR TREATING HEART FAILURE

(75) Inventors: Lilip Lau, Los Altos, CA (US); William Hartigan, Fremont, CA (US); Anuja Patel, San Jose, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 733 days.

This patent is subject to a terminal disclaimer.

(21) Appl. No.: 10/754,264

(22) Filed: Jan. 9, 2004

(65) Prior Publication Data

US 2004/0143156 A1    Jul. 22, 2004

(51) Int. Cl.
*A61B 19/00* (2006.01)

(52) U.S. Cl. ..................................... 600/37
(58) Field of Classification Search ............. 600/16, 600/37; 36/50.1, 110; 385/100; 128/897–898; 606/157; 623/66.1, 3; 601/11, 152

See application file for complete search history.

(56) References Cited

U.S. PATENT DOCUMENTS

| | | | |
|---|---|---|---|
| 2,826,193 A | 3/1958 | Vineberg | |
| 3,464,322 A | 9/1969 | Pequignol | |
| 3,513,836 A | 5/1970 | Sausse | |
| 3,587,567 A | 6/1971 | Schiff | |
| 3,613,672 A | 10/1971 | Schiff | |
| 3,855,715 A * | 12/1974 | Johnson | 36/50.1 |
| 3,966,401 A | 6/1976 | Hancock et al. | |
| 3,983,863 A | 10/1976 | Janke et al. | |
| 3,988,782 A | 11/1976 | Dardik et al. | |
| 4,011,947 A | 3/1977 | Sawyer | |
| 4,048,990 A | 9/1977 | Goetz | |
| 4,065,816 A | 1/1978 | Sawyer | |
| 4,108,161 A | 8/1978 | Samuels et al. | |
| 4,192,293 A | 3/1980 | Asrican | |
| 4,211,325 A | 7/1980 | Wright | |
| 4,217,706 A * | 8/1980 | Vartanian | 36/110 |

(Continued)

FOREIGN PATENT DOCUMENTS

DE    3831 540 A1    4/1989

(Continued)

OTHER PUBLICATIONS

Chiu, Ray C.-J. *Using Skeletal Muscle for Cardiac Assistance*, Scientific American Science & Medicine, Nov./Dec. 1994.

(Continued)

*Primary Examiner*—John P Lacyk
(74) *Attorney, Agent, or Firm*—Fulwider Patton LLP

(57) ABSTRACT

A cardiac harness is configured to fit about a portion of a patient's heart so as to exert a compressive force on the heart during at least a portion of the cardiac cycle. The harness can be constructed of a plurality of individual modules assembled ex vivo or in vivo. The modules can have different physical characteristics, such as having different compliance, and may or may not include spring hinges. Portions of a cardiac harness can be connected to each other using a coupling mechanism such as, for example, a zip coupler.

27 Claims, 27 Drawing Sheets

U.S. PATENT DOCUMENTS

| | | |
|---|---|---|
| 4,261,342 A | 4/1981 | Aranguren Duo |
| 4,306,318 A | 12/1981 | Mano et al. |
| 4,372,293 A | 2/1983 | Vijil-Rosales |
| 4,403,604 A | 9/1983 | Wilkinson et al. |
| 4,428,375 A | 1/1984 | Ellman |
| 4,512,471 A | 4/1985 | Kaster et al. |
| 4,536,893 A | 8/1985 | Parravicini |
| 4,545,783 A | 10/1985 | Vaughan |
| 4,628,937 A | 12/1986 | Hess et al. |
| 4,630,597 A | 12/1986 | Kantrowitz et al. |
| 4,665,906 A | 5/1987 | Jervis |
| 4,690,134 A | 9/1987 | Snyders |
| 4,697,703 A | 10/1987 | Will |
| 4,750,619 A | 6/1988 | Cohen et al. |
| 4,821,723 A | 4/1989 | Baker, Jr. et al. |
| 4,827,932 A | 5/1989 | Ideker et al. |
| 4,834,707 A | 5/1989 | Evans |
| 4,838,288 A | 6/1989 | Wright et al. |
| 4,840,626 A | 6/1989 | Linsky et al. |
| 4,863,016 A | 9/1989 | Fong et al. |
| 4,878,890 A | 11/1989 | Bilweis |
| 4,936,857 A | 6/1990 | Kulik |
| 4,957,477 A | 9/1990 | Lundbäck |
| 4,960,424 A | 10/1990 | Grooters |
| 4,973,300 A | 11/1990 | Wright |
| 4,976,730 A | 12/1990 | Kwan-Gett |
| 5,031,762 A | 7/1991 | Heacox |
| 5,057,117 A | 10/1991 | Atweh |
| 5,067,957 A | 11/1991 | Jervis |
| 5,087,243 A | 2/1992 | Avitall |
| 5,098,369 A | 3/1992 | Heilman et al. |
| 5,106,386 A | 4/1992 | Isner et al. |
| 5,119,804 A | 6/1992 | Anstadt |
| 5,131,905 A | 7/1992 | Grooters |
| 5,150,706 A | 9/1992 | Cox et al. |
| 5,169,381 A | 12/1992 | Snyders |
| 5,186,711 A | 2/1993 | Epstein |
| 5,190,546 A | 3/1993 | Jervis |
| 5,192,314 A | 3/1993 | Daskalakis |
| 5,197,978 A | 3/1993 | Hess |
| 5,256,132 A | 10/1993 | Snyders |
| 5,279,539 A | 1/1994 | Bohan et al. |
| 5,290,217 A | 3/1994 | Campos |
| 5,336,254 A | 8/1994 | Brennen et al. |
| 5,344,442 A | 9/1994 | Deac |
| 5,352,184 A | 10/1994 | Goldberg et al. |
| 5,356,432 A | 10/1994 | Rutkow et al. |
| 5,366,460 A | 11/1994 | Eberbach |
| 5,383,840 A | 1/1995 | Heilman et al. |
| 5,385,156 A | 1/1995 | Oliva |
| 5,385,229 A | 1/1995 | Bittmann et al. |
| 5,385,528 A | 1/1995 | Wilk |
| 5,405,360 A | 4/1995 | Tovey |
| 5,429,584 A | 7/1995 | Chiu |
| 5,433,727 A | 7/1995 | Sideris |
| 5,456,711 A | 10/1995 | Hudson |
| 5,460,962 A | 10/1995 | Kemp |
| 5,500,015 A | 3/1996 | Deac |
| 5,507,779 A | 4/1996 | Altman |
| 5,509,428 A | 4/1996 | Dunlop |
| 5,524,633 A | 6/1996 | Heaven et al. |
| 5,533,958 A | 7/1996 | Wilk |
| 5,534,024 A | 7/1996 | Rogers et al. |
| 5,545,210 A | 8/1996 | Hess et al. |
| 5,558,617 A | 9/1996 | Heilman et al. |
| 5,571,215 A | 11/1996 | Sterman et al. |
| 5,582,616 A | 12/1996 | Bolduc et al. |
| 5,584,803 A | 12/1996 | Stevens et al. |
| 5,593,424 A | 1/1997 | Northrup III |
| 5,593,441 A | 1/1997 | Lichtenstein et al. |
| 5,597,378 A | 1/1997 | Jervis |
| 5,603,337 A | 2/1997 | Jarvik |
| 5,607,477 A | 3/1997 | Schindler et al. |
| 5,647,372 A | 7/1997 | Tovey et al. |
| 5,647,380 A | 7/1997 | Campbell et al. |
| 5,695,525 A | 12/1997 | Mulhauser et al. |
| 5,702,343 A | 12/1997 | Alferness |
| 5,713,954 A | 2/1998 | Rosenberg et al. |
| 5,727,569 A | 3/1998 | Benetti et al. |
| 5,749,839 A | 5/1998 | Kovacs |
| 5,782,746 A | 7/1998 | Wright |
| 5,800,528 A | 9/1998 | Lederman et al. |
| 5,814,097 A | 9/1998 | Sterman et al. |
| 5,824,028 A | 10/1998 | Knisley |
| 5,836,311 A | 11/1998 | Borst et al. |
| 5,848,962 A | 12/1998 | Feindt et al. |
| 5,849,005 A | 12/1998 | Garrison et al. |
| 5,853,422 A | 12/1998 | Huebsch et al. |
| 5,865,791 A | 2/1999 | Whayne et al. |
| 5,876,432 A | 3/1999 | Lau et al. |
| 5,889,910 A * | 3/1999 | Igl et al. .................... 385/100 |
| 5,904,690 A | 5/1999 | Middleman et al. |
| 5,910,124 A | 6/1999 | Rubin |
| 5,927,284 A | 7/1999 | Borst et al. |
| 5,948,019 A | 9/1999 | Shu et al. |
| 5,957,977 A | 9/1999 | Melvin |
| 5,961,440 A | 10/1999 | Schweich, Jr. et al. |
| 5,976,069 A | 11/1999 | Navia et al. |
| 5,979,456 A | 11/1999 | Magovern |
| 5,984,857 A | 11/1999 | Buck et al. |
| 5,990,378 A | 11/1999 | Ellis |
| 6,007,486 A | 12/1999 | Hunt et al. |
| 6,015,378 A | 1/2000 | Borst et al. |
| 6,024,096 A | 2/2000 | Buckberg |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,076,013 A | 6/2000 | Brennan et al. |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,095,968 A | 8/2000 | Snyders |
| 6,110,100 A | 8/2000 | Talpade |
| 6,117,159 A | 9/2000 | Huebsch et al. |
| 6,117,979 A | 9/2000 | Hendriks et al. |
| 6,123,662 A | 9/2000 | Alferness et al. |
| 6,125,852 A | 10/2000 | Stevens et al. |
| 6,126,590 A | 10/2000 | Alferness |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,166,184 A | 12/2000 | Hendriks et al. |
| 6,169,922 B1 | 1/2001 | Alferness et al. |
| 6,174,279 B1 | 1/2001 | Girard |
| 6,179,791 B1 | 1/2001 | Krueger |
| 6,183,411 B1 | 2/2001 | Mortier et al. |
| 6,190,408 B1 | 2/2001 | Melvin |
| 6,193,648 B1 | 2/2001 | Krueger |
| 6,206,820 B1 | 3/2001 | Kazi et al. |
| 6,214,047 B1 | 4/2001 | Melvin |
| 6,217,894 B1 | 4/2001 | Sawhney et al. |
| 6,221,103 B1 | 4/2001 | Melvin |
| 6,224,540 B1 | 5/2001 | Ledermann et al. |
| 6,230,714 B1 | 5/2001 | Alferness et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,282,445 B1 | 8/2001 | Reinhardt et al. |

| | | |
|---|---|---|
| 6,287,250 B1 | 9/2001 | Peng et al. |
| 6,293,906 B1 | 9/2001 | Vanden Hoek et al. |
| 6,306,141 B1 | 10/2001 | Jervis |
| 6,312,725 B1 | 11/2001 | Wallace et al. |
| 6,352,710 B2 | 3/2002 | Sawhney et al. |
| 6,360,749 B1 | 3/2002 | Jayaraman |
| 6,375,608 B1 | 4/2002 | Alferness |
| 6,390,976 B1 | 5/2002 | Spence et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,432,039 B1* | 8/2002 | Wardle .................... 600/37 |
| 6,451,025 B1 | 9/2002 | Jervis |
| 6,482,146 B1 | 11/2002 | Alferness et al. |
| 6,517,570 B1 | 2/2003 | Lau et al. |
| 6,537,203 B1 | 3/2003 | Alferness et al. |
| 6,544,168 B2 | 4/2003 | Alferness |
| 6,547,821 B1 | 4/2003 | Taylor et al. |
| 6,564,094 B2 | 5/2003 | Alferness et al. |
| 6,567,699 B2 | 5/2003 | Alferness et al. |
| 6,569,082 B1 | 5/2003 | Chin |
| 6,572,533 B1 | 6/2003 | Shapland et al. |
| 6,575,921 B2 | 6/2003 | Vanden Hoek et al. |
| 6,582,355 B2 | 6/2003 | Alferness et al. |
| 6,587,734 B2 | 7/2003 | Okuzumi |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,633,780 B1 | 10/2003 | Berger |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,689,048 B2 | 2/2004 | Vanden Hoek et al. |
| 6,695,769 B2 | 2/2004 | French et al. |
| 6,699,259 B2 | 3/2004 | Fogarty et al. |
| 6,701,929 B2 | 3/2004 | Hussein |
| 6,702,732 B1 | 3/2004 | Lau et al. |
| 6,723,041 B2* | 4/2004 | Lau et al. ................. 600/37 |
| 6,730,016 B1 | 5/2004 | Cox et al. |
| 6,755,779 B2 | 6/2004 | Vanden Hoek et al. |
| 6,759,431 B2 | 7/2004 | Hunter et al. |
| 6,818,018 B1 | 11/2004 | Sawhney |
| 6,833,408 B2 | 12/2004 | Sehl et al. |
| 6,876,887 B2 | 4/2005 | Okuzumi |
| 2001/0029314 A1 | 10/2001 | Alferness et al. |
| 2001/0047122 A1 | 11/2001 | Vanden Hoek et al. |
| 2002/0007216 A1 | 1/2002 | Melvin |
| 2002/0022880 A1 | 2/2002 | Melvin |
| 2002/0032364 A1 | 3/2002 | Lau et al. |
| 2002/0068849 A1 | 6/2002 | Schweich, Jr. et al. |
| 2002/0077524 A1 | 6/2002 | Schweich, Jr. et al. |
| 2002/0082647 A1 | 6/2002 | Alferness et al. |
| 2002/0091296 A1 | 7/2002 | Alferness |
| 2002/0103511 A1 | 8/2002 | Alferness et al. |
| 2002/0151950 A1 | 10/2002 | Okuzumi |
| 2003/0060674 A1 | 3/2003 | Gifford III et al. |
| 2003/0060677 A1 | 3/2003 | French et al. |
| 2003/0060895 A1 | 3/2003 | French et al. |
| 2003/0199733 A1 | 10/2003 | Shapland et al. |
| 2003/0199955 A1 | 10/2003 | Struble et al. |
| 2003/0229265 A1 | 12/2003 | Girard et al. |
| 2004/0133069 A1 | 7/2004 | Shapland et al. |
| 2004/0143155 A1* | 7/2004 | Lau et al. ................. 600/37 |
| 2004/0171907 A1 | 9/2004 | Alferness et al. |
| 2004/0171908 A1 | 9/2004 | Alferness et al. |

FOREIGN PATENT DOCUMENTS

| | | |
|---|---|---|
| DE | 38 31 540 C2 | 6/1993 |
| DE | 295 17 393 U1 | 3/1996 |
| EP | 0 370 931 A1 | 5/1990 |
| EP | 0 280 564 B1 | 6/1993 |
| EP | 0 583 012 B1 | 7/1996 |
| EP | 0 791 330 A3 | 8/1997 |
| EP | 0 919 193 A1 | 6/1999 |
| FR | 2 527 435 | 12/1983 |
| FR | 2 645 739 | 10/1990 |
| GB | 2 115 287 A | 9/1983 |
| GB | 2 209 678 A | 5/1989 |
| JP | 60-203250 | 10/1985 |
| JP | 1-145066 | 6/1989 |
| JP | 1-271829 | 10/1989 |
| SU | 1009457 A | 4/1983 |
| SU | 1734767 A1 | 5/1992 |
| WO | WO 91/19465 | 12/1991 |
| WO | WO 95/06447 | 3/1995 |
| WO | WO 96/04852 | 2/1996 |
| WO | WO 96/40356 | 12/1996 |
| WO | WO 97/20505 | 6/1997 |
| WO | WO 97/24101 | 7/1997 |
| WO | WO 98/03213 | 1/1998 |
| WO | WO 98/14136 | 4/1998 |
| WO | WO 98/26738 | 6/1998 |
| WO | WO 98/29041 | 7/1998 |
| WO | WO 98/58598 | 12/1998 |
| WO | WO 99/11201 | 3/1999 |
| WO | WO 99/30647 | 6/1999 |
| WO | WO 99/44534 | 9/1999 |
| WO | WO 99/44680 | 9/1999 |
| WO | WO 99/53977 | 10/1999 |
| WO | WO 99/56655 | 11/1999 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/13722 | 3/2000 |
| WO | WO 00/16700 | 3/2000 |
| WO | WO 00/18320 | 4/2000 |
| WO | WO 00/28912 | 5/2000 |
| WO | WO 00/28918 | 5/2000 |
| WO | WO 00/42919 | 7/2000 |
| WO | WO 00/45735 | 8/2000 |
| WO | WO 00/48795 | 8/2000 |
| WO | WO 00/62727 | 10/2000 |
| WO | WO 00/74769 | 12/2000 |
| WO | WO 01/17437 | 3/2001 |
| WO | WO 01/21098 | 3/2001 |
| WO | WO 01/91667 A2 | 6/2001 |
| WO | WO 01/50981 | 7/2001 |
| WO | WO 01/67985 | 9/2001 |
| WO | WO 01/85061 | 11/2001 |
| WO | WO 01/95830 | 12/2001 |
| WO | WO 01/95831 | 12/2001 |
| WO | WO 01/95832 | 12/2001 |
| WO | WO 02/13726 | 2/2002 |
| WO | WO 02/19917 | 3/2002 |
| WO | WO 03/026483 | 4/2003 |
| WO | WO 03/026484 | 4/2003 |
| WO | WO 03/026485 | 4/2003 |

OTHER PUBLICATIONS

David A. Kass, M.D., et al., *Reverse Remodeling From Cardiomyoplasty in Human Heart Failure*, Circulation, vol. 91, No. 9, May 1, 1995.

Howard R. Levin, M.D., et al., *Reversal of Chronic Ventricular Dilation in Patients With End-Stage Cardiomyopathy by Prolonged Mechanical Unloading*, Circulation, vol. 91, No. 11, Jun. 1995.

Eli R. Capouya, M.D., et al, *Girdling Effect on Nonstimulated Cardiomyoplasty on Left Ventricular Function, Society of Thoracic Surgeons*, pp. 867-871, 1993.

Bencini, Adriano, M.D.,The "Pneumomassage" of the Heart, *Surgery*, vol. 39, No. 3, Mar. 1956.

Paling, D.F., *Warp Knitting Technology*, 1970.

Edie, Richard N., M.D., et al.,Surgical Repair of Single Ventricle, *The Journal of Thoracic and Cardiovascular Surgery*, vol. 66, No. 3, pp. 350-360, Sep. 1972.

McGoon, Dwight C., M.D., et al., Correction of the Univentricular Heart Having Two Atriovantricular Valves, *The Journal of Thoracic and Cardiovascular Surgery*, vol. 74, No. 2, pp. 218-226, Aug. 1977.

Doly, Donald B., et al., Septation of the Univentricular Heart: Transatrial Approach, *The Journal of Thoracic and Cardiovascular Surgery*, vol. 78, No. 3, pp. 424-430, Sep. 1979.

Schetky, L., McDonald, Shap—Memory Alloys, *Scientific American*, vol. 241, No. 5, pp. 74-82, Nov. 1979.

Melton, K.N., et al., Alloys With Two-Shape Memory Effect, *Mechanical Engineering*, pp. 42-43, Mar. 1980.

Feldt, Robert H., M.D., et al., Current Status of the Septation Procedure for Univentricular Heart, *The Journal of Thoracic and Cardiovascular Surgery*, vol. 82, No. 1, pp. 93-97, Jul. 1981.

Carpentier, A., et al., Myocardial Substitution With Stimulated Skeletal Muscle: First Successful Clinical Case. *The Lancet*, Jun. 1, 1985.

Anstadt, George L. et al., Direct Mechanical Ventricular Actuation: A Review, *Resuscitation*, pp. 7-23, 1991.

Anstadt, Mark P., M.D., et al., Pulsatile Reperfusion After Cardiac Arrest Improves Neurologic Outcome, *American Surgery*, vol. 214, No. 4, pp. 478-490, Oct. 1991.

Schumacker, Harris B., Jr., Chapter 21: Cardiace Aneurysms, *The Evolution of Cardiac Surgery*, pp. 159-165, 1992.

Savage, Edward B., M.D., et al., Repair of Left Ventricular Aneurysm, *The Journal of Thoracic and Cardiovascular Surgery*, vol. 104, No. 3, pp. 752-762, Sep. 1992.

Carpentier, Alain, M.D. Ph.D., et al., Dynamic Cardiomyoplasty at Seven Years, *The Journal of Thoracic and Cardiovascular Surgery*, vol. 106, No. 1, pp. 42-54, Jul. 1993.

Chekanov, Valeri, M.D., Ph.D., Nonstimulated Cardiomyoplasty Wrap Attenuated the Degree of Left Ventricular Enlargement, *Annals of Thoracic Surgeons*, vol. 57, pp. 1684-1690, 1997.

Vaynblat, Mikhail, M.D., et al., Cardiac Binding in Experimental Heart Failure, Annals of Thoracic Surgery (Abstract), Supplement to *Circulation*, vol. 92, Suppl. 1, 1995.

Chaudhry, Pervaiz A., M.D., et al., Acute Ventricular Reduction with Acorn's Cardiac Support Device Prevents Progressive Left Ventricular Dysfunction and Remodeling in Dogs With Advanced Heart Failure, *Cardiothoracic Surgery*, pp. 146-148, 1996.

Oh, Joong, Hwan, M.D., et al., Mechanisms of Dynamic Cardiomyoplasty: Current Concepts, *Journal of Cardiac Surgery*, vol. 11, pp. 194-199, 1996.

Badhwar, Vinay, Power Generation From Four Skeletal Muscle Configurations Design Implications for a Muscle Powered Cardiac Assist Device, *ASAIO Journal*, vol. 43, pp. M651-M657, 1997.

Westaby, Stephen, et al., *Landmarks in Cardiac Surgery*, pp. 198-199, 1997.

Cox, James L., Left Ventricular Aneurysms: Pathophysiologic Observations and Standard Resection, *Seminars in Thoracic and Cardiovascular Surgery*, vol. 9, No. 2, pp. 113-122, Apr. 1997.

Coletta, C., et al., Prognostic Value of Left Ventricular Volume Responding During Dobutamine Stress Echocardiography, *European Heart Journal*, vol. 18, pp. 1599-1603, Oct. 1997.

Capomolla, Soccorso, M.D., et al., Dobutamine and Nitroprusside Infusion in Patients With Severe Congestive Heart Failure: Hemodynamic Improvement by Discordan Effects on Mitral Regurgitation, Left Atrial Function, and Ventricular Function, *American Heart Journal*, 1089-1098, Dec. 1997.

Oh, Joong Hwan, The Effects of Prosthetic Cardiac Binding and Adynamic Cardiomyoplasty in a Model of Dilated Cardiomyopathy, *The Journal of Thoracic and Cardiovascular Surgery*, vol. 116, No. 1, pp. 148-153, 1998.

Cohn, Jay N., M.D., Preventing Congestive Heart Failure, *American Family Physician*, 6 pages, Apr. 15, 1998.

Cohn, Jay N., M.D., Structural Basis for Heart Failure: Ventricular Remodeling and Its Pharmacological Inhibition *Circulation*, vol. 91, No. 10, pp. 2504-2507, May 15, 1995.

Gaudron, Peter, M.D., et al., *Progressive Left Ventricular Dysfunction and Remodeling After Myocardial Infarction*, Circulation, vol. 87, pp. 755-763, Mar. 1993.

Pfeiffer, Marc A., M.D., et al., Ventricular Remodeling After Myocardial Infarction: Experimental Observations and Clinical Implications, *Circulation*, vol. 81, No. 4, pp. 1161-1172, Apr. 1990.

Guasp, Francisco Torrent, *Una protesis contentiva para el tratamiento de le microcardiopatia dilatads, Revista Española de Cardiologia*, vol. 51, No. 7, Jul. 1998.

Power, J.M., et al., Passive Ventricular Constraint Amends the Course of Heart Failure: A Study in an Ovine Model of Dilated Cardiomyopathy, *Cardiovascular Research*, vol. 44, pp. 549-555, 1999.

Frazier, O.H., M.D., et al., Left Ventricular Assist System as a Bridge to Myocardial Recovery, *Annals of Thoracic Surgery*, vol. 68, pp. 734-741, 1999.

Melvin, David B., Ventricular Radium Reduction Without Resection: A Computational Analysis, *ASAIO Journal*, pp. 160-165, 1999.

*ABSTRACTS—Heart Failure*, JACC Feb. 1999.

Raman, Jai S., FRACS, et al., Ventricular Containment as an Adjunctive Procedure in Ischemic Cardiomyopathy: Early Results, *Annals of Thoracic Surgery*, vol. 70, pp. 1124-1126, Jan. 2000.

McCarthy, Patrick M., et al., *Device Based Left Ventricular Shape Change Immediately Reduces Left Ventricular Volume and Increases Ejection Fraction in a Pacing Induced Cardiomyopathy Model in Dogs*, JACC, Feb. 2000.

Chaudhry, Pervaiz A., M.D., et al., Passive Epicardial Containment Prevents Ventricular Remodeling in Heart Failure, *Annals of Thoracic Surgeons*, vol. 70, pp. 1275-1280, 2000.

Acorn Cardiovascular, Inc., *CSD Specifications Acorn Cardiac Support Device*, 2000.

*Heart "jacket" could help stop heart failure progression.* Clinicia, No. 916, Jul. 2000.

Acorn Cardiovascular, Inc., *CorCap™Cardiac Device* Pamphlet, Jun. 2001.

*Medtronic's InSync Cardiac Resynchronization Therapy Device Approved by FDA*, (Press Release) Aug. 28, 2001.

Acorn Cardiovascular, Inc., *Acorn Highlights: ESC*, Schedule, Sep. 2001.

Oz, Mehmet C., M.D., Passive Ventricular Constraint for the Treatment of Congestive Heart Failure, *Annals of Thoracic Surgery*, vol. 71, pp. 5185-5187, 2001.

Abstract Supplement, *European Heart Journal*, vol. 22, Sep. 2001.

Gorman, J., Self-Sutures: New Material Knots Up On Its Own, *Science News*, vol. 161, p. 262, Apr. 27, 2002.

Mann, Douglas L., M.D., *Basic Mechanisms of Remodeling and Reverse Remodeling*, presented at 6th Annual Scientific Meeting of the Heart Failure Society of America, Sep. 24, 2002.

Bocchi, Edimar a., M.D., Arrhythmias and Sudden Death After Dynamic Cardiomyoplasty, *Circulation*, vol. 90, No. 5, Part 2, pp. 11-107 thru 11-111, Nov. 1994.

Chachques, Juan C., M.D., Study of Muscular and Ventricular Function in Dynamic Cardiomyoplasty: A Ten-Year Follow-Up, *The Journal of Heart and Lung Transplantation*, vol. 16, No. 8, pp. 854-868, Aug. 1997.

Dullum, Mercedes K.C., M.D., et al., *Less Invasive Surgical Management of Heart Failure by Cardiac Support Device Implantation on the Beating Heart*. The Heart Surgery Forum, #2001-1818, pp. 361-363, Jan. 4-7, 2001.

Macris, Michael P. M.D., et al., Minimally Invasive Access of the Normal Preicardium: Initial Clinical Experience with a Novel Device, *Clinical Cardiology*, vol. 22 (Suppl. 1), pp. 1-36 thru 1-39, 1999.

Thakur, Ranjan K., M.D., et al., Latissimus Dorsi Dynamic Cardiomyoplasty: Role of Combined ICD Implantation, *Journal of Cardiac Surgery*, vol. 10, pp. 295-297, 1995.

Wharton, J. Marcus, et al., Electrophysiological Effects of Monophasic and Biphasic Stimuli in Normal and Infarcted Dogs, *PACE*, vol. 13, pp. 1158-1172, Sep. 1990.

Shabetai, Ralph, The Role of the Pericardium in the Pathophysiology of Heart Failure, *Congestive Heart Failure*, Second Edition, Chapter 9, pp. 157-187, 2000.

Cohn, Jay N., M.D., The Management of Chronic Heart Failure, *The New England Journal of Medicine*, vol. 335, No. 7, pp. 490-498, Aug. 15, 1996.

\* cited by examiner

DEVICE FOR TREATING HEART FAILURE

RELATED APPLICATIONS

This application claims priority to U.S. Provisional Application No. 60/322,089, which was filed on Sep. 10, 2001, the entirety of which is hereby incorporated by reference.

BACKGROUND OF THE INVENTION

1. Field of the Invention

The present invention relates to a device for treating heart failure. More specifically, the invention relates to a cardiac harness configured to be fit around at least a portion of a patient's heart.

2. Description of the Related Art

Congestive heart failure ("CHF") is characterized by the failure of the heart to pump blood at sufficient flow rates to meet the metabolic demand of tissues, especially the demand for oxygen. One characteristic of CHF is remodeling of at least portions of a patient's heart. Remodeling involves physical changes to the size, shape and thickness of the heart wall. For example, a damaged left ventricle may have some localized thinning and stretching of a portion of the myocardium. The thinned portion of the myocardium often is functionally impaired, and other portions of the myocardium attempt to compensate. As a result, the other portions of the myocardium may expand so that the stroke volume of the ventricle is maintained notwithstanding the impaired zone of the myocardium. Such expansion may cause the left ventricle to assume a somewhat spherical shape.

Cardiac remodeling often subjects the heart wall to increased wall tension or stress, which further impairs the heart's functional performance. Often, the heart wall will dilate further in order to compensate for the impairment caused by such increased stress. Thus, a vicious cycle can result, in which dilation leads to further dilation and greater functional impairment.

Historically, congestive heart failure has been managed with a variety of drugs. Devices have also been used to improve cardiac output. For example, left ventricular assist pumps help the heart to pump blood. Multi-chamber pacing has also been employed to optimally synchronize the beating of the heart chambers to improve cardiac output. Various skeletal muscles, such as the latissimus dorsi, have been used to assist ventricular pumping. Researchers and cardiac surgeons have also experimented with prosthetic "girdles" disposed around the heart. One such design is a prosthetic "sock" or "jacket" that is wrapped around the heart.

Although some of the above-discussed devices hold promise, there remains a need in the art for a device for treating CHF to prevent a remodeled heart from further remodeling and/or help reverse remodeling of a diseased heart.

SUMMARY OF THE INVENTION

In accordance with one aspect of the present invention, a cardiac harness is configured to fit about a patient's heart. The harness comprises a plurality of individual modules that are assembled together to form the harness.

In accordance with another aspect, the present invention provides a cardiac harness configured to fit about a patient's heart. A first module of the harness extends along a first portion of a circumference of the harness. A second module extends along a second portion of the circumference of the harness. The first and second modules are connected to one another.

In accordance with still another aspect, the present invention provides a cardiac harness configured to fit about a patient's heart. A zip coupler is configured to selectively draw a first portion of the harness adjacent to a second portion of the harness.

In accordance with a further aspect of the present invention, a method of making a cardiac harness comprises providing a plurality of modules and connecting the modules to one another to form the harness.

In accordance with a still further aspect, the present invention provides a method of treating a diseased heart. A cardiac harness is provided and is configured to fit about a patient's heart. The harness has a first end and a second end that are adapted to be coupled to one another. At least a portion of the harness is rolled about an axis. The rolled harness is placed adjacent a portion of the patient's heart, and the harness is unrolled so that the unrolled harness fits about the heart.

In accordance with yet another aspect, the present invention provides a cardiac harness comprising a plurality of modules adapted to be coupled to each other. Each of the modules comprises a plurality of spring elements.

In accordance with still another aspect of the present invention, a cardiac harness is provided having a plurality of modules. Each module has a first edge, a second edge, and a zip coupling mechanism. The zip coupling mechanism selectively draws the first and second edges adjacent to one another.

In accordance with a further aspect of the present invention, a cardiac harness is provided. The cardiac harness is configured to fit about a patient's heart, and has a base portion, an apex portion and a medial portion between the apex and base portions. The apex portion has a plurality of spiral shaped elongate members. Each spiral shaped elongate member is connected at one end to the medial portion and at the other end to a terminal member.

In accordance with a still further aspect of the present invention, a cardiac harness is provided having a base portion, an apex portion and a medial portion between the apex and base portions. The base portion has interconnected spring elements that are oriented so that the collective spring force around the circumference of the base portion is in a first direction. The medial portion has interconnected spring elements oriented so that the collective spring force around at least a portion of the circumference of the medial portion is in a second direction substantially different than the first direction.

In accordance with yet a further aspect, the present invention provides a cardiac harness having a central cavity for receiving a portion of a patient's heart so that the harness contacts the wall of the heart substantially throughout the cavity. The harness has a plurality of protrusions extending inwardly so that interference between the protrusion and the wall of the heart aids retention of the harness on the heart.

Further features and advantages of the present invention will become apparent to one of skill in the art in view of the Detailed Description of Preferred Embodiments which follows, when considered together with the attached drawings and claims.

BRIEF DESCRIPTION OF THE DRAWINGS

FIG. 19a schematically shows an end view of edges of the modules of FIG. 19 aligned with each other and showing a zip coupler.

DETAILED DESCRIPTION OF PREFERRED EMBODIMENTS

Figure 1:
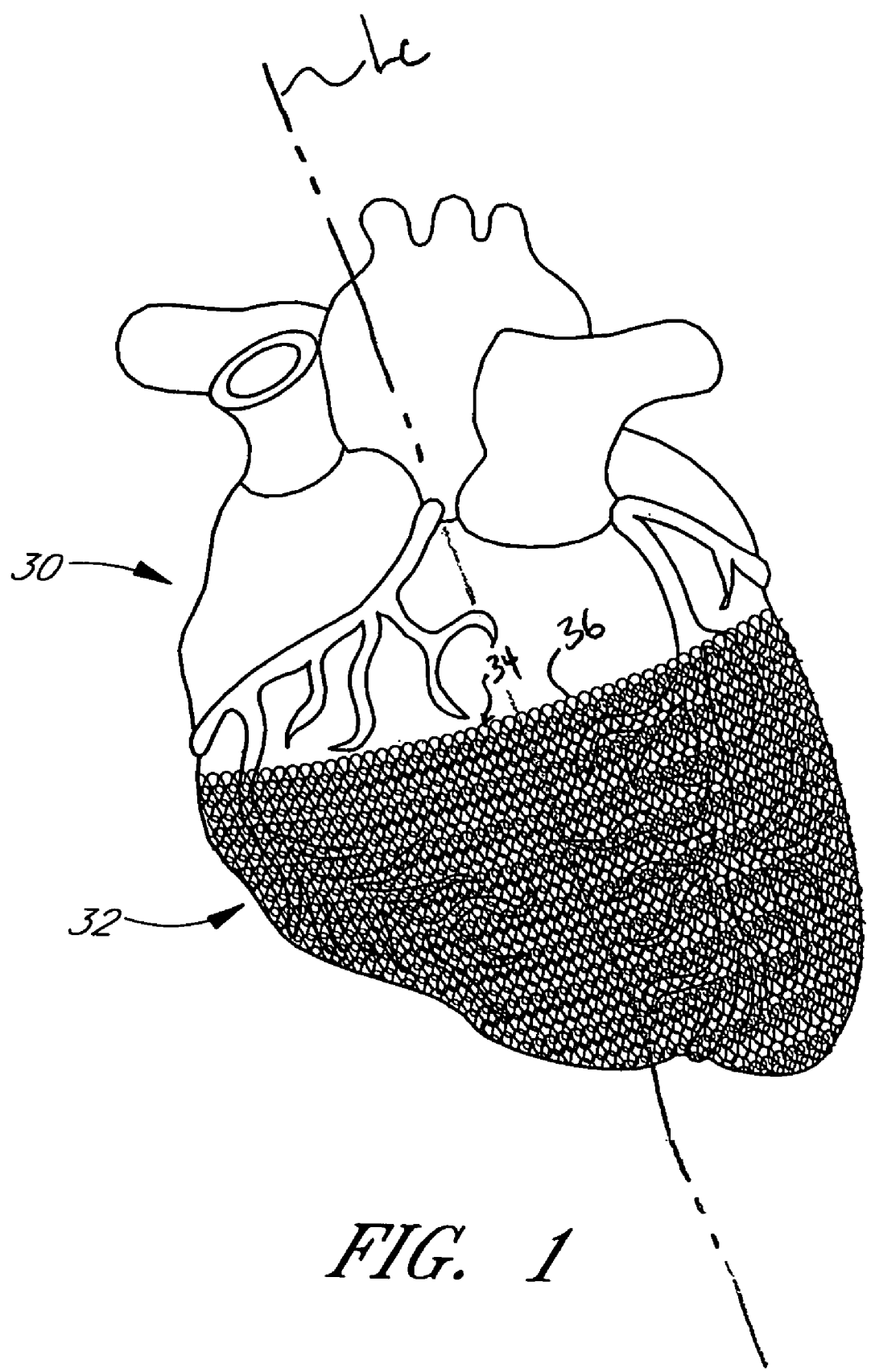
FIG. 1 is a schematic view of a heart with a cardiac harness placed thereon.

FIG. 1 illustrates a mammalian heart 30 with a cardiac harness 32 applied thereto. The illustrated cardiac harness 32 comprises a series of hinges or spring elements that circumvent the heart and, collectively, apply a mild compressive force on the heart so as to alleviate wall stresses. As discussed in Applicant's co-pending application entitled "Expandable Cardiac Harness For Treating Congestive Heart Failure," Ser. No. 09/634,043, which was filed on Aug. 8, 2000, the entirety of which is hereby expressly incorporated by reference, remodeling of a diseased heart can be resisted or even reversed by alleviating the wall stresses in such a heart.

The term "cardiac harness" as used herein is a broad term that refers to a device fit onto a patient's heart to apply a compressive force on the heart during at least a portion of the cardiac cycle. Other devices that are intended to be fit onto a heart and are referred to in the art as "girdles," "socks," "jackets," or the like are included within the meaning of "cardiac harness."

Figure 2A:
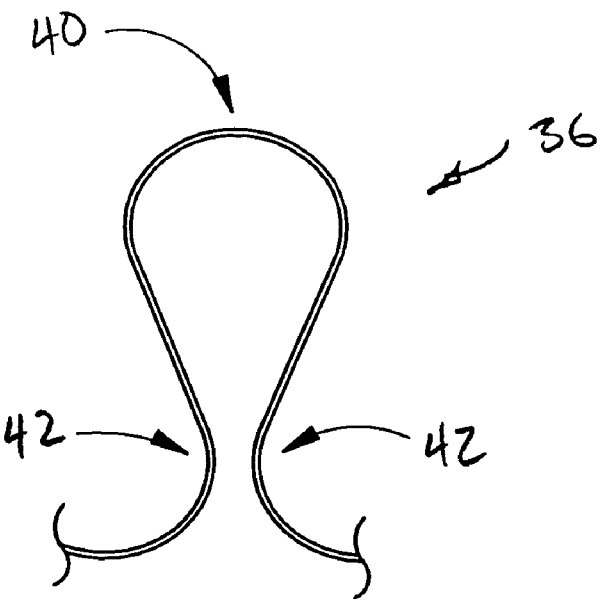
FIGS. 2A-2B illustrate a spring hinge in a relaxed position and under tension.
Figure 2B:
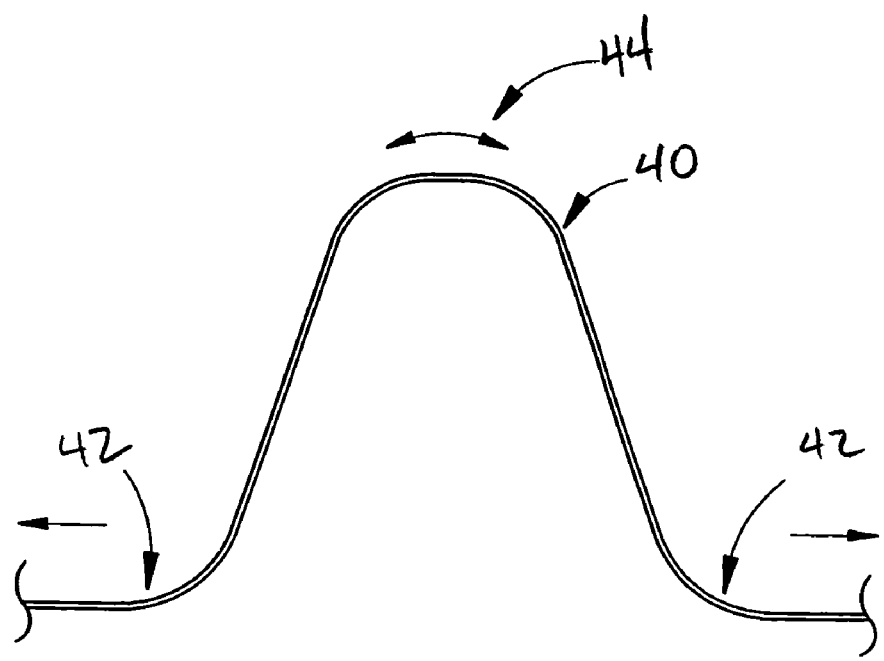

The cardiac harness 32 illustrated in FIG. 1 comprises at least one undulating strand 34 comprising a series of spring elements 36 referred to as hinges or spring hinges that are configured to deform as the heart 30 expands during filling. Each hinge 36 provides substantially unidirectional elasticity, in that it acts in one direction and does not provide much elasticity in the direction perpendicular to that direction. FIG. 2A shows one embodiment of a hinge member 36 at rest. The hinge member 36 has a central portion 40 and a pair of arms 42. As the arms 42 are pulled, as shown in FIG. 2B, a bending moment 44 is imposed on the central portion 40. Thus, there is a force resisting deformation. A typical strand 34 of hinges 36 comprises a series of such hinges 36, which are adapted to elastically expand and retract in the direction of the strand 34.

Figure 3:
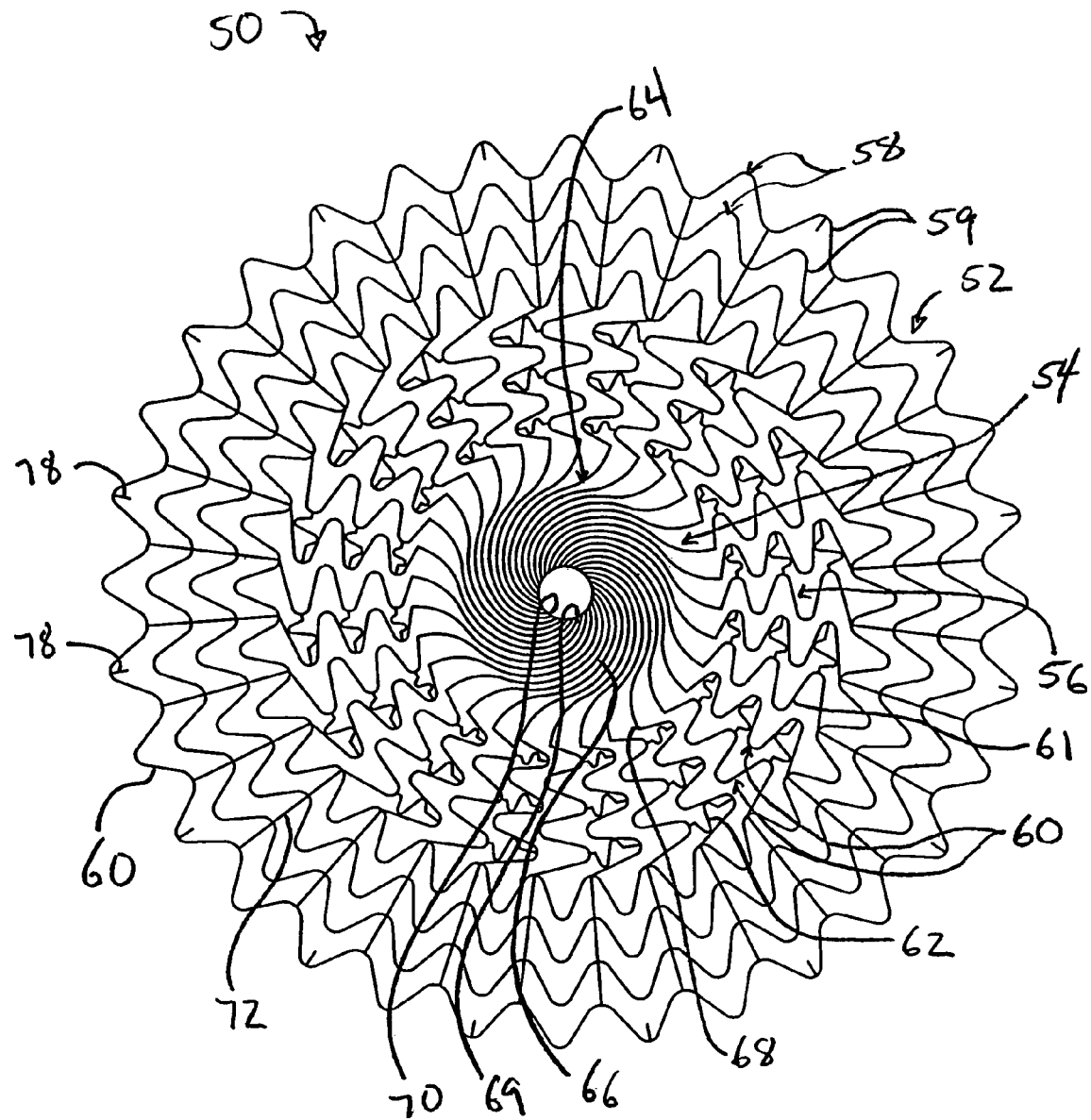
FIG. 3 shows an embodiment of a cardiac harness that has been cut out of a flat sheet of material.
Figure 4:
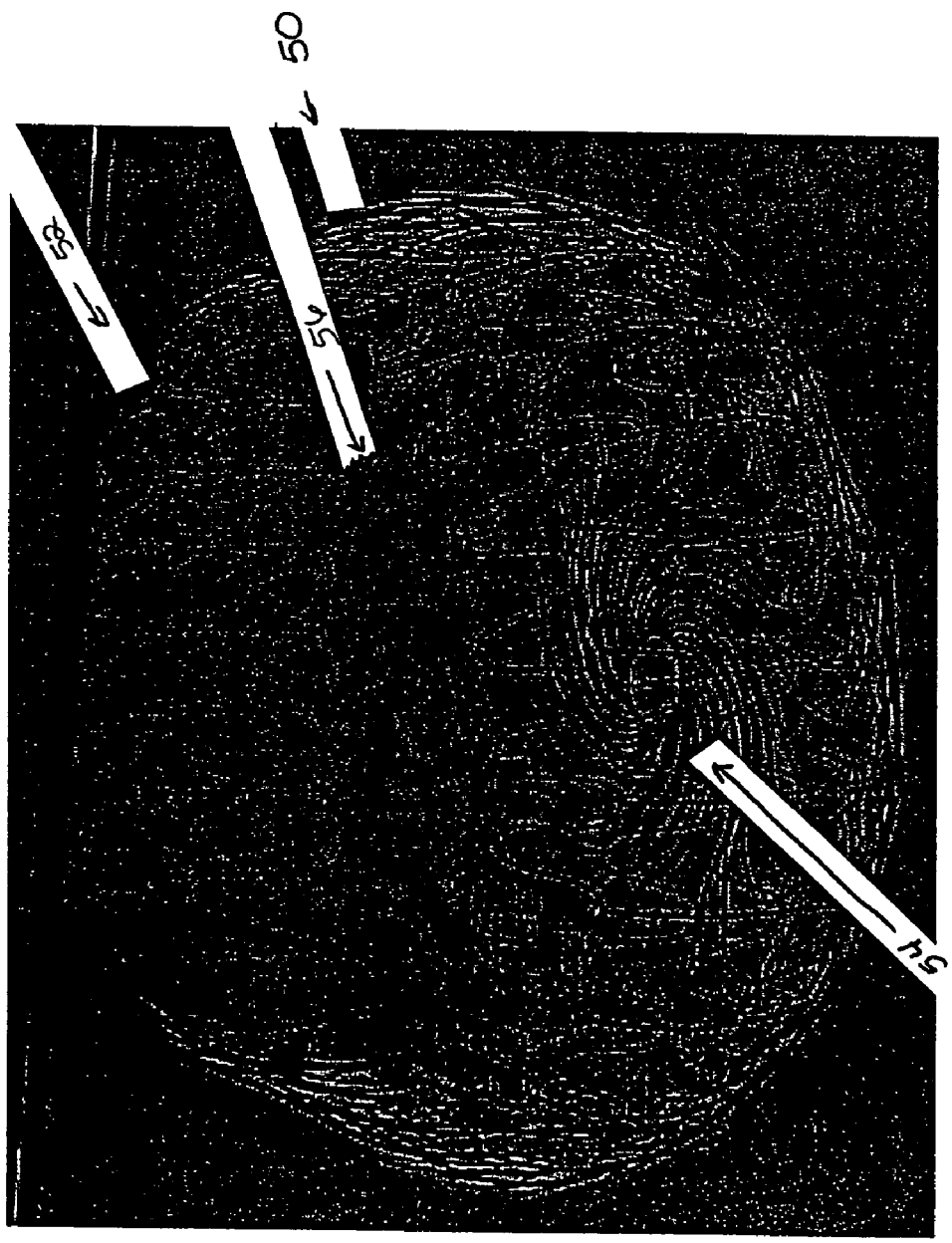
FIG. 4 shows the cardiac harness of FIG. 3 formed into a shape configured to fit about a heart.

FIGS. 3 and 4 illustrate an embodiment of a cardiac harness 50, shown at two points during manufacture of the harness. In the illustrated embodiment, the harness 50 has been etched from a thin sheet of Nitinol, which is a superelastic material that also exhibits shape memory properties. The flat sheet of material is draped over a form, die or the like so that it takes on the shape of at least a portion of a heart (see FIG. 4).

With continued reference to FIGS. 3 and 4, the harness 50 comprises a base portion 52, which is sized and configured to generally engage and fit onto a base region of the heart 30; an apex portion 54, which is sized and shaped to generally engage and fit on an apex region of the heart; and a medial portion 56 between the base and apex portions 52, 54.

As shown in FIGS. 3 and 4, the harness 50 comprises several strands 34 or rows of undulating wire comprising spring hinges 36. The strands of spring hinges in the illustrated embodiment are oriented in different directions and are configured differently in the various portions of the harness. For example, in the base portion 52 of the harness 50, strands 58 are oriented so that the spring elements 59 will expand and contract in a direction generally transverse to a longitudinal axis Lc of the heart 30. As such, a collective spring force around the circumference of the base portion 52 is directed generally transverse to the longitudinal axis Lc.

In the medial portion 56, strands 60 are oriented so that spring elements 61 expand and contract in a generally longitudinal direction. Additionally, several of the longitudinally-extending strands 60 are connected to one another by interconnecting spring elements 62, which connect the strands 60 but still allow relative movement therebetween. However, some longitudinal strands 60 are not connected to adjacent longitudinal strands 60; these unconnected longitudinal strands can move freely relative to one another in the transverse direction. As shown, the medial portion 56 includes a combination of spring directions. Of course, the longitudinally-directed springs 61 exert a spring force in the longitudinal direction, and the transversely-directed springs 62 exert a spring force in the transverse direction. Collectively, however, the spring hinges 61, 62 in the medial portion 56 exert a spring force around the circumference of the harness 50 that is directed in a medial direction between the longitudinal and transverse directions.

In the apex portion 54, an "archimedes spiral" 64 configuration of the harness allows compliant expansion and deformation of the harness in more than one direction. The archimedes spiral 64 comprises a plurality of spiral shaped elongate members 66 disposed adjacent one another. A first end 68 of each of the elongate members 66 is connected to the medial portion 56. In the illustrated embodiment, the elongate member 66 is coextensive with a longitudinally-oriented spring hinge 61. A second end 69 of each elongate member 66 is connected to a terminal member 70. As such, a plurality of spiral shaped elongate members 66 are connected to a terminal member 70. The illustrated archimedes spiral 64 in the apex portion 54 has relatively high compliance, and is most compliant in a longitudinal direction.

In a mammalian heart, the heart muscle cells in the base region tend to expand and contract in a generally transverse direction during pumping of the heart. In the apex region, the heart muscles tend to expand and contract in a generally longitudinal direction. Between the apex and base regions of the heart, the heart muscles generally expand in directions between the longitudinal and transverse directions. As such, the arrangement of spring hinges in the base, medial and apex portions 52, 56, 54 of the harness 50 illustrated in FIGS. 3 and 4 is specially adapted to accommodate the natural expansion and contraction of heart muscle. The spring elements 59, 61 in each portion are oriented generally in the directions of the pericardial muscle expansion in the corresponding region of the heart so as to more precisely resist excessive expansion of the heart. Accordingly, the harness 50 helps to decrease the workload of the heart 30, enabling the heart to more effectively pump blood through the patient's body. Decreasing its workload also gives the heart an opportunity to heal itself.

With continued reference to FIGS. 3 and 4, the strands 58 of spring elements 59 in the base portion 52 are connected one to another by interconnecting elements 72. In this manner, when the rows/strands 58 expand and contract in a transverse direction, the interconnecting elements 72 prevent the harness 50 from growing smaller in a longitudinal direction, or foreshortening. This provides an important benefit, because foreshortening of the harness 50 in the base portion 52 could create a force that squeezes the heart longitudinally. Of course, this could make the heart smaller in a longitudinal direction, even as the heart expands circumferentially. This could increase the sphericity of the heart to a degree that is undesired and may be inefficient for pumping. By eliminating or resisting foreshortening, the present harness helps to maintain the natural shape of the heart and/or limits the sphericity of the heart.

In another embodiment, the interconnecting elements comprise compliant springs. Such compliant interconnecting elements help maintain the relative positions of the strands but allow for longitudinal expansion and contraction of the heart with little or no resistance by the harness. Thus, compliant interconnecting elements also help the harness avoid foreshortening.

As discussed above, the cardiac harness embodiment illustrated in FIGS. 3 and 4 is etched out of a flat sheet of Nitinol. After forming the flat sheet into a desired shape as shown in FIG. 4, the Nitinol material preferably is annealed by being placed in an oven at about 475° C. for about 20 minutes. The harness 50 then is removed from the oven and quenched in cold water. The harness retains or "memorizes" the annealed shape. Due to the shape memory properties of Nitinol, the harness can then be deformed, even plastically deformed, at certain temperatures, but when the deformed harness is returned to a shape memory temperature range, the harness will resume its annealed shape. This can be especially helpful in embodiments wherein the harness is delivered via minimally-invasive surgical methods. In such embodiments, the harness is compressed and/or folded so as to be more easily introduced into the body, but expands to its memory shape when exposed to the body's warm internal temperatures.

Although the embodiments of FIGS. 1-4 are constructed of Nitinol, it is to be understood that various designs and materials can be used for a cardiac harness. For example, suitable materials include metals and polymers such as, for example, Nitinol, other shape memory materials including metal alloys or polymers such as oligo (e-caprolactone) dimethacrylate, stainless steel, Elgiloy™, titanium, tantalum, polyimide, polyethylene, nylon, polypropylene, polycarbonate, ePTFE and polyester.

In the embodiment illustrated in FIGS. 3-4, a flat sheet of Nitinol has been photochemically etched and then bent into a desired shape. It is to be understood that any of a variety of methods of manufacture can be used to create a sheet that can later be formed into a harness, or even to directly create a harness that generally complements the shape of a heart without having to be deformed. Such manufacturing processes can include, for example, casting, mechanical machining, cutting with a waterjet, EDM, milling, laser cutting, and stamping. After the harness has been created, the harness preferably is polished by an electrochemical or a mechanical method.

One aspect of the cardiac harness 50 shown in FIGS. 3 and 4 is that by etching the harness as a single unitary structure, there are no overlapping wires or filaments, and no connections, such as welds, are needed. As such, the spring hinges operate without overlapping and contacting the other spring hinges. Thus, wear incident to friction created by such overlapping materials is avoided. Also, stress concentrations that could result from welds and other mechanical connections are avoided.

In another embodiment, drawn wire can be formed into undulating strands of spring hinges that collectively form a cardiac harness. A cardiac harness 32 formed of drawn wire can be configured so that adjacent rows 34 of spring hinges 32 overlap and are interwoven with one another as shown in the embodiment of FIG. 1. In other embodiments, the cardiac harness is configured so that the rows of spring hinges made of drawn wire do not overlap or contact adjacent spring hinges. Preferably, the wire comprises drawn Nitinol wire that is annealed so as to "remember" its undulating shape.

Embodiments of cardiac harnesses can be provided in various sizes, shapes and configurations. As discussed above, the harness 50 embodiment illustrated in FIGS. 3 and 4 comprises a generally circular sheet that is deformed into a generally conical shape to accommodate a patient's heart. In another embodiment, the harness is not quite circular when in sheet form, so that when the sheet is deformed into a generally conical shape, a distance from base to apex is longer on one side of the harness than on another. In still other embodiments, the heart can comprise a ribbon or fan comprising a series of adjacent undulating rows of spring hinges.

The compliance of a cardiac harness can be custom-tailored as desired during manufacture by using special configurations of the spring elements. Not every spring element in the harness need have the same compliance characteristics. For example, some spring elements may have longer arms than other spring elements. The longer-armed hinges likely will be more compliant than the shorter-armed hinges. Another way to vary compliance for different areas of the harness is for some spring elements to be thicker than others. The thicker springs will resist deformation with a greater force. Depending upon placement of the spring elements, one portion or area of the harness can be more compliant than other areas of the harness.

In one embodiment, a first set of springs deform readily upon application of a first threshold force, and a second set of springs begin to deform only when a second force threshold has been reached. Thus, the cardiac harness exhibits a compliance curve that is very compliant over a first range of strain but becomes dramatically stiffer upon reaching a chosen threshold of strain. This can be helpful if it is desired to exert more compressive force on a larger heart than on a smaller, possibly-less-diseased heart.

With continued reference to FIGS. 3 and 4, an anchoring mechanism can be included in the harness 50. The anchoring mechanism helps retain the harness in position on the heart 30. As discussed above, the harness 50 is configured to be fit about a portion of the patient's heart. The portion of the heart fits within a central cavity 74 of the harness 50. In the illustrated embodiment, the outermost row 76 of undulations includes a series of barbs 78 extending from some of the spring elements 59. The barbs 78 can be bent inwardly so that they extend into the central cavity 74 of the harness 50. When the harness 50 is placed upon a heart, each barb 78 at least partially engages or pierces the heart wall, thus resisting movement of the harness downwardly toward the apex of the heart and off of the heart muscle. In the illustrated embodiment the barbs 78 are integrally formed with the harness 50 as it is etched.

Figure 5:
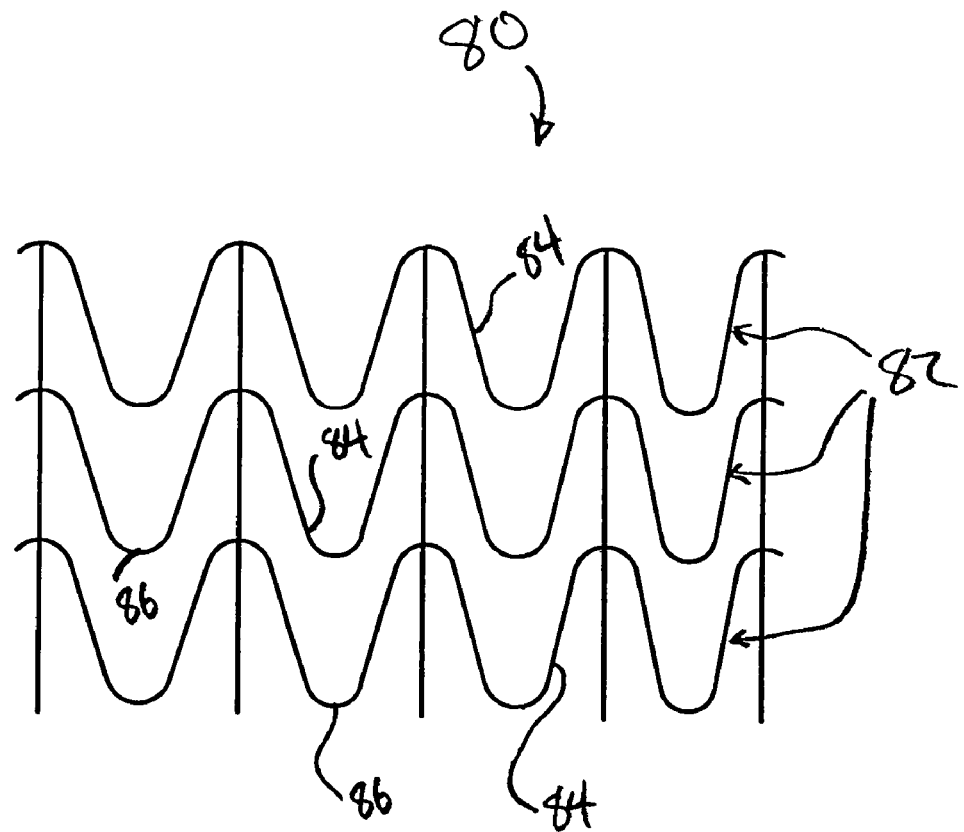
FIG. 5 illustrates a portion of a cardiac harness having spring hinges configured in accordance with one embodiment.
Figure 6:
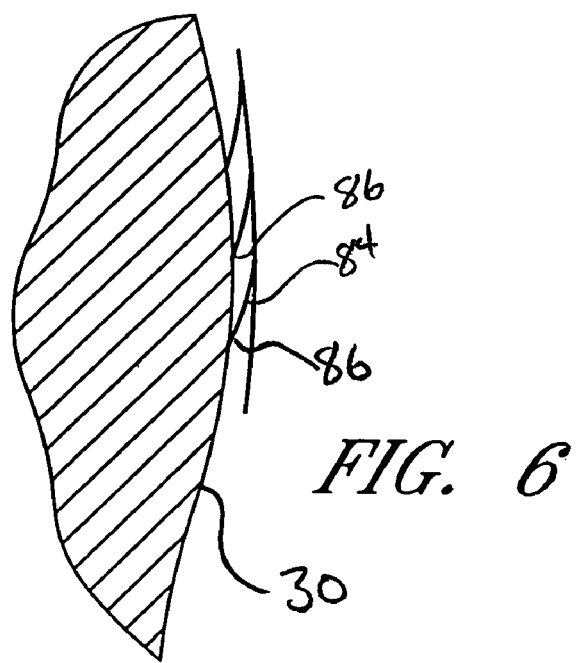
FIG. 6 schematically shows the portion of the harness of FIG. 5 wherein a center portion of the spring hinges frictionally engages a surface of the heart.

Another embodiment of an anchoring apparatus is represented in FIGS. 5 and 6. FIG. 5 shows a portion of a cardiac harness 80 which includes rows 82 of spring hinges 84. Each spring hinge 84 has a bottom center portion 86, which can be bent inwardly so as to protrude into the central cavity of the harness 80. As shown schematically in FIG. 6, when the harness 80 is placed against the patient's heart 30, the inwardly bent bottom center portions 86 engage the epicardium of the heart 30. Although the center portions 86 of the hinge 84 are not sharp and do not penetrate cardiac tissue like the barbs, their engagement with the heart wall creates significant resistance so that the interference generated by many bottom center portions 86 working together resists movement of the harness 80 toward the apex and off of the heart.

In a still further embodiment, a portion of the harness can be configured to protrude into the central cavity by providing one or more spring hinges that are stiffer than surrounding spring hinges. Since such stiffer spring hinges will not be as compliant as the surrounding harness, they will have more of a tendency to protrude into the central cavity and thus provide additional interference between the harness and the wall of the heart.

Figure 7:
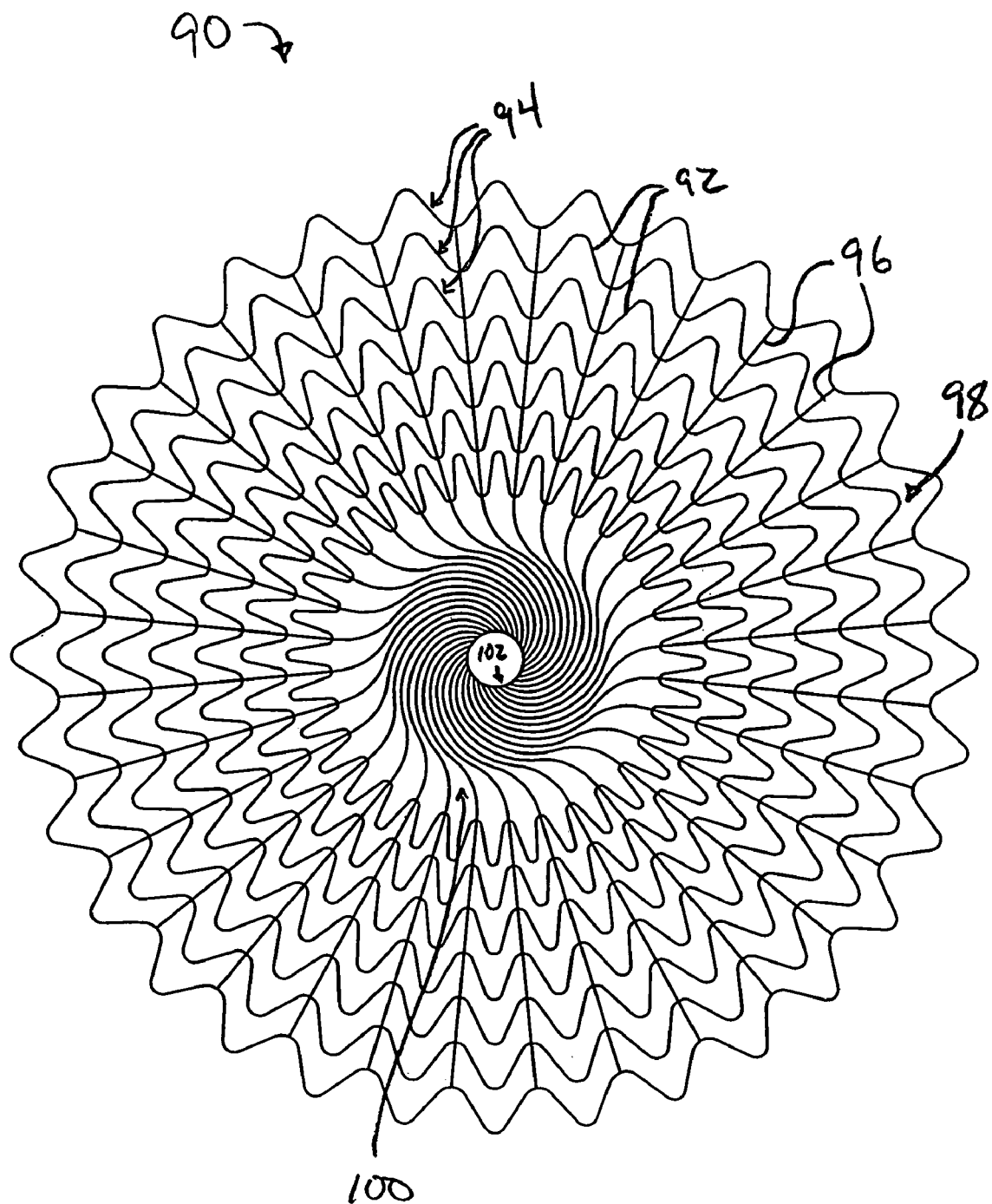
FIG. 7 illustrates another embodiment of a cardiac harness cut out of a flat sheet of material.
Figure 8:
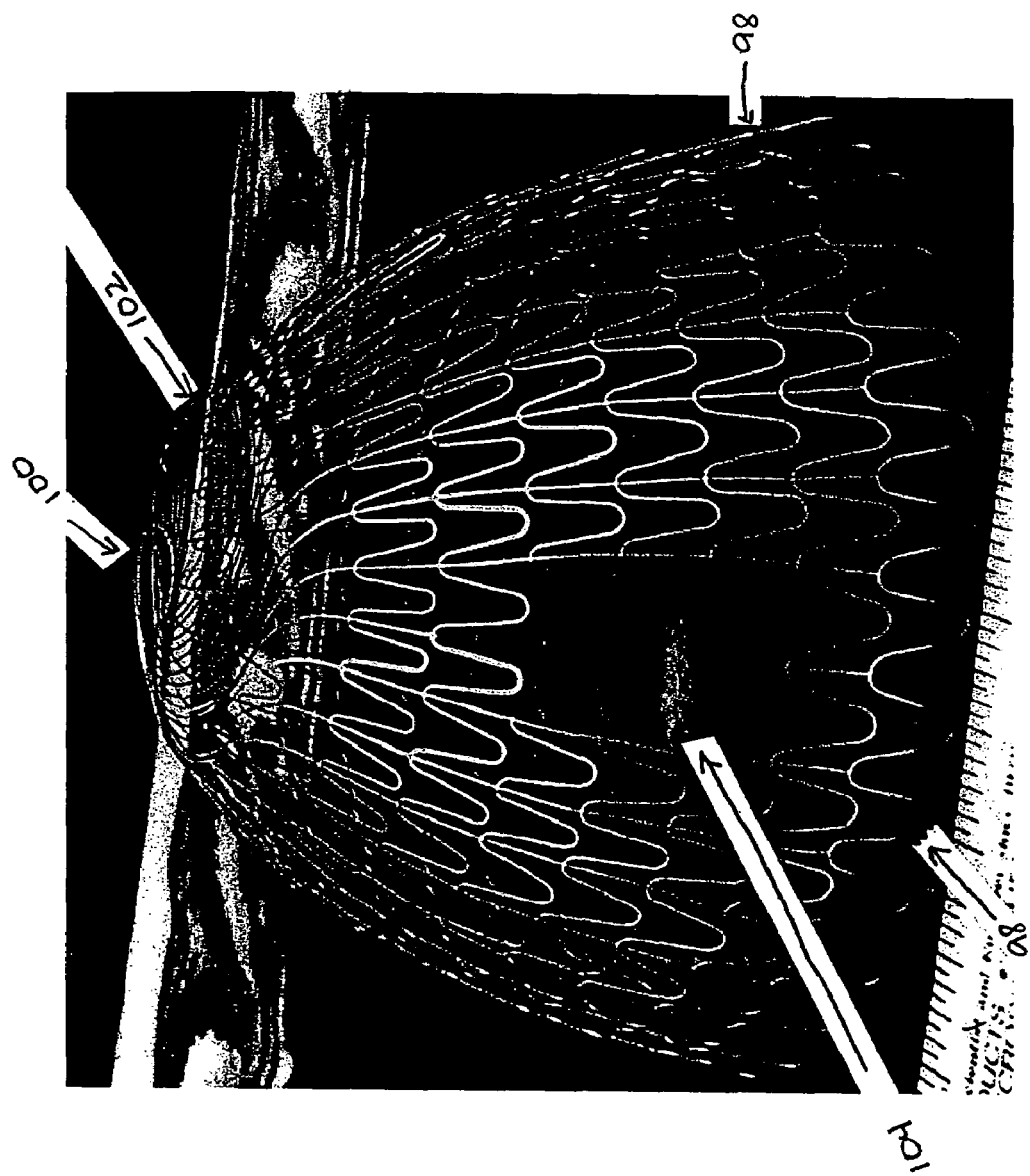
FIG. 8 shows an embodiment of a cardiac harness having a window formed therethrough.
Figure 9:
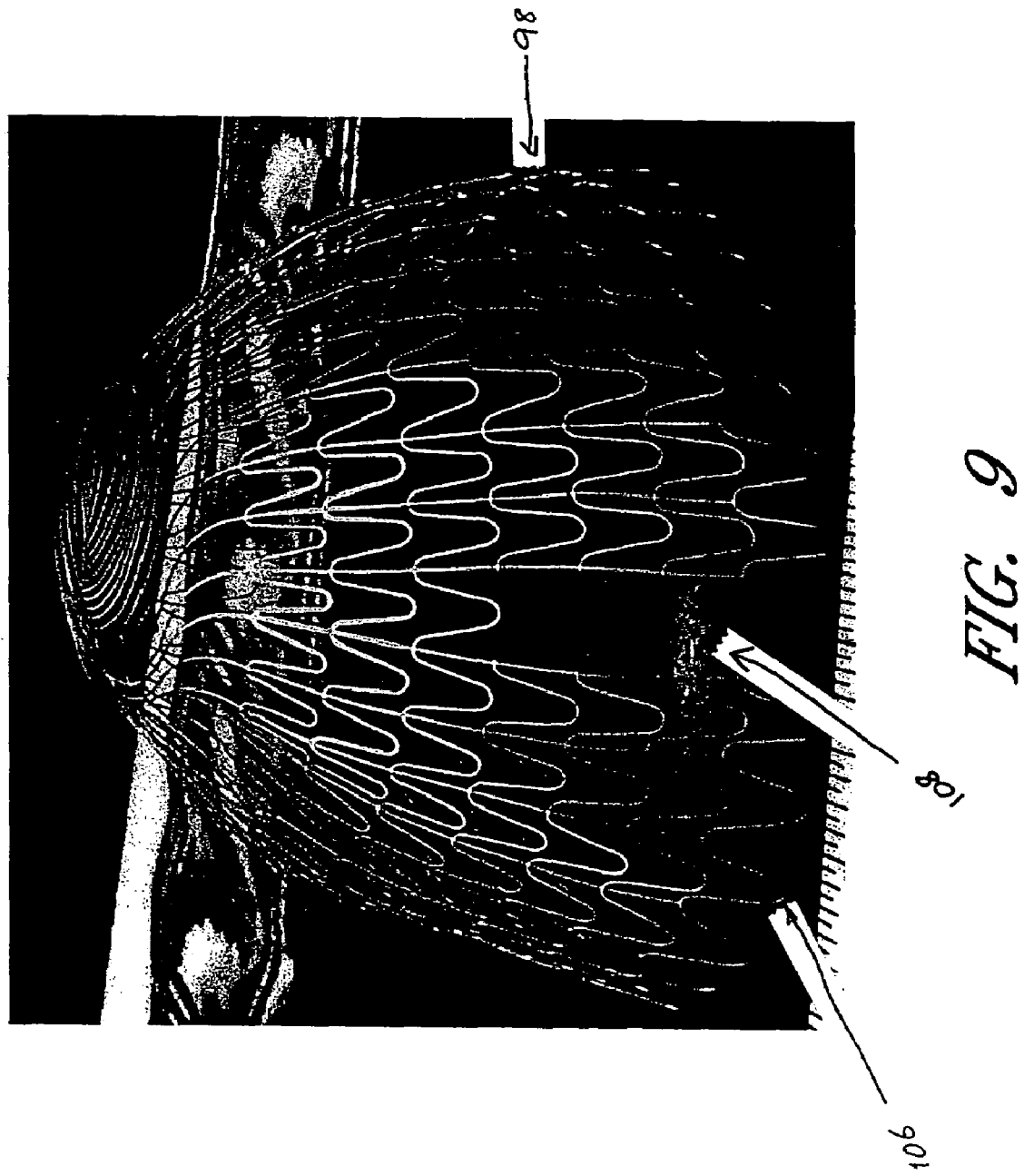
FIG. 9 shows an embodiment of a cardiac harness having a slot formed therethrough.

FIG. 7 shows another embodiment of an etched unitarily-formed cardiac harness 90 prior to being formed into a desired shape. As can be seen in the figure, the illustrated embodiment comprises a different arrangement and configuration of spring elements 92 than is found in FIG. 1 or 3. Adjacent rows 94 of spring elements 92 are connected by substantially straight interconnecting elements 96, which extend from the base 98 to the apex 100 and bend into an archimedes spiral 102 arrangement in the apex portion 100 of the device. FIGS. 8 and 9 each illustrate embodiments wherein the harness 90 of FIG. 7 is molded into a form adapted to engage a heart.

As discussed above, various configurations of spring elements 92 can advantageously be used in a cardiac harness. Such configurations may include several rows 94 of spring elements 92 that may or may not be interconnected together by connecting elements 96. Further, such connecting elements may also include spring elements or even an elastic material so that the adjacent rows of spring hinges are moveable relative to one another.

FIGS. 8 and 9 each illustrate embodiments wherein a portion of a harness 90 has been removed. In FIG. 8, a window 104 is formed through a side of the harness, but the outermost strand 106 of the harness in the base remains undisturbed. In FIG. 9, the outermost strand of the harness has also been interrupted. Thus, a slot 108 is formed through a side of the harness, and the outermost strand 106 no longer completely circumvents the heart. The window 104 and slot 106 embodiments provide access for a surgeon to perform certain surgical procedures, such as, for example, cardiac bypass, or installing and working with coronary artery grafts. In some embodiments, it may be preferable to reattach portions of the harness that have been removed so as to regain the elasticity and support that was removed with the window or slot portions.

Installation Methods and Apparatus

Any suitable method can be employed to install a cardiac harness on a patient's heart. For example, the harness can be slid over the heart during an open thoracic surgery procedure or during a surgery using minimally-invasive methods. However, hearts, especially beating hearts, are slippery and can be difficult to work with. Additionally, in order for the harness to apply a compressive force on the heart when installed, the harness preferably is somewhat smaller than the patient's heart when the spring hinges are at rest. As the harness is drawn over the heart during installation, the harness squeezes the heart, and the heart may tend to slide away from the harness, making it difficult to install the harness onto the heart.

In accordance with another embodiment, a cardiac harness can be installed on the heart without having to slide an intact harness over the heart. Instead, a harness such as that shown in FIGS. 4, 8 and 9 is modified so as to be split or cut longitudinally along at least a portion of the length of the harness from the base to the apex. As such, the harness can be fit loosely adjacent and around the heart without squeezing the heart during installation. Once placed adjacent the heart, the harness can be wrapped about the heart to restore the circumferential continuity of the harness. The edges of the harness at the longitudinal split can be reattached in any known manner, such as by sutures, clips, hooks or by a zip coupler as discussed below.

Figure 10:
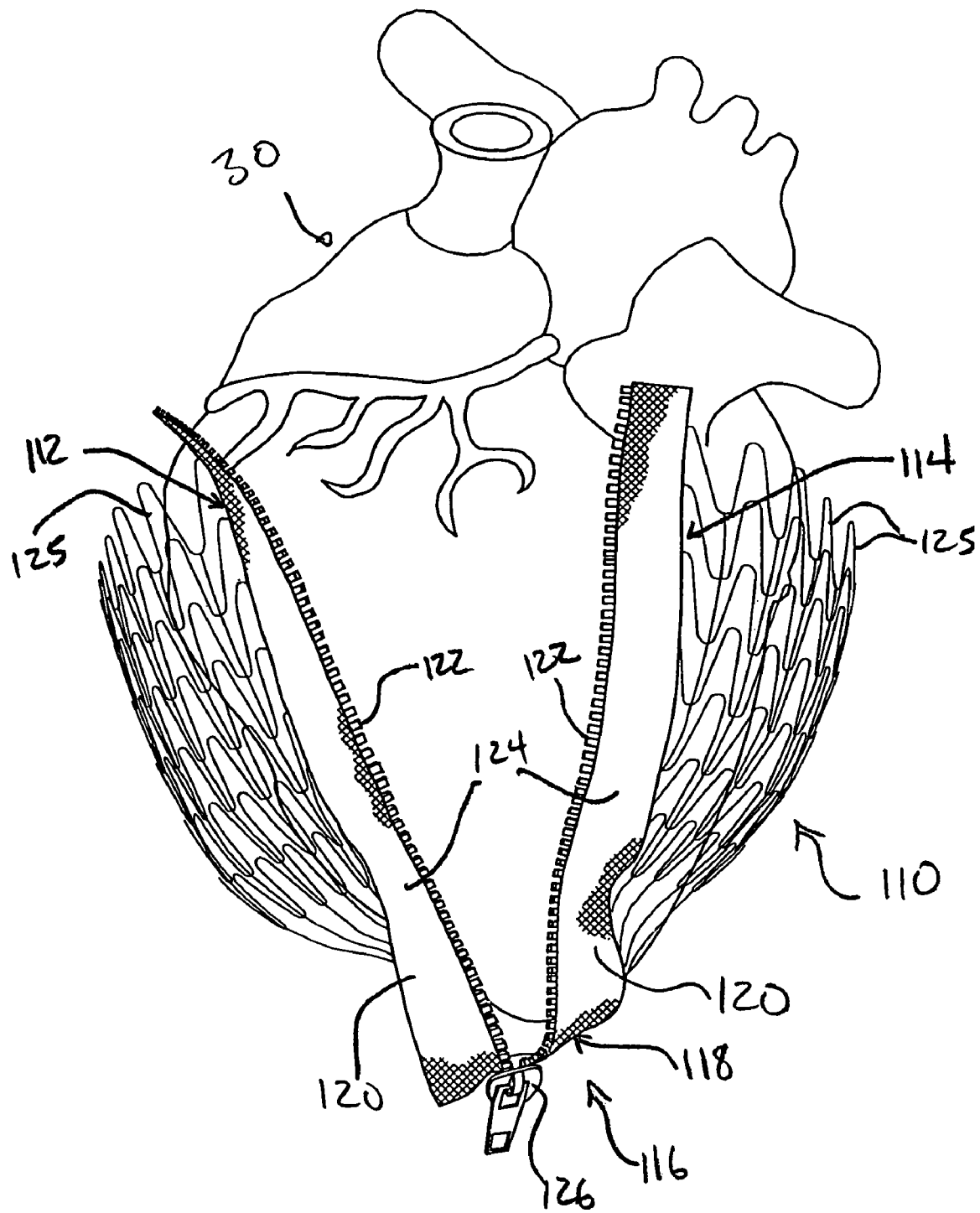
FIG. 10 schematically shows an embodiment of a cardiac harness fit loosely about a heart.
Figure 11:
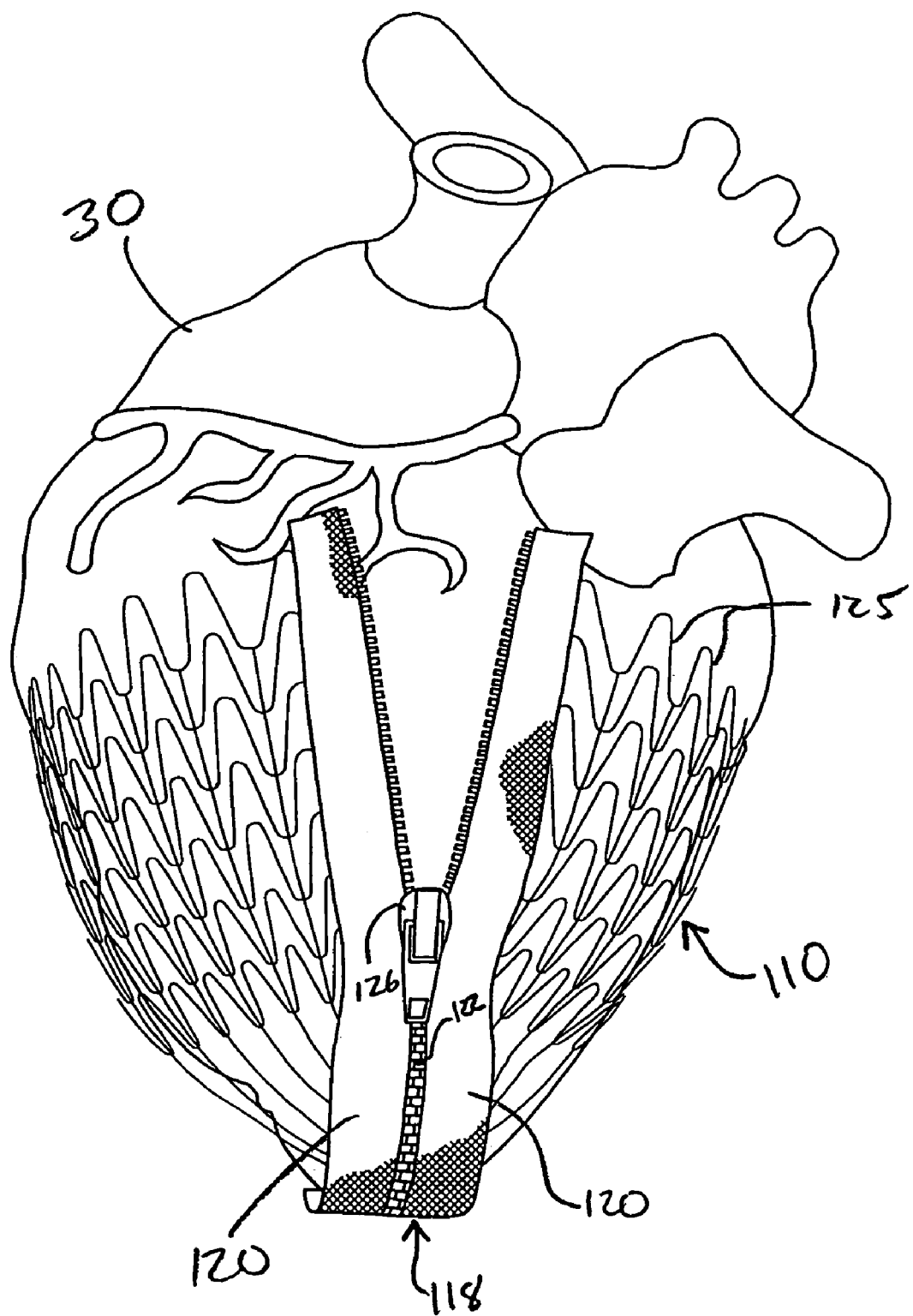
FIG. 11 shows the cardiac harness of FIG. 10 being tightened around the heart.
Figure 12:
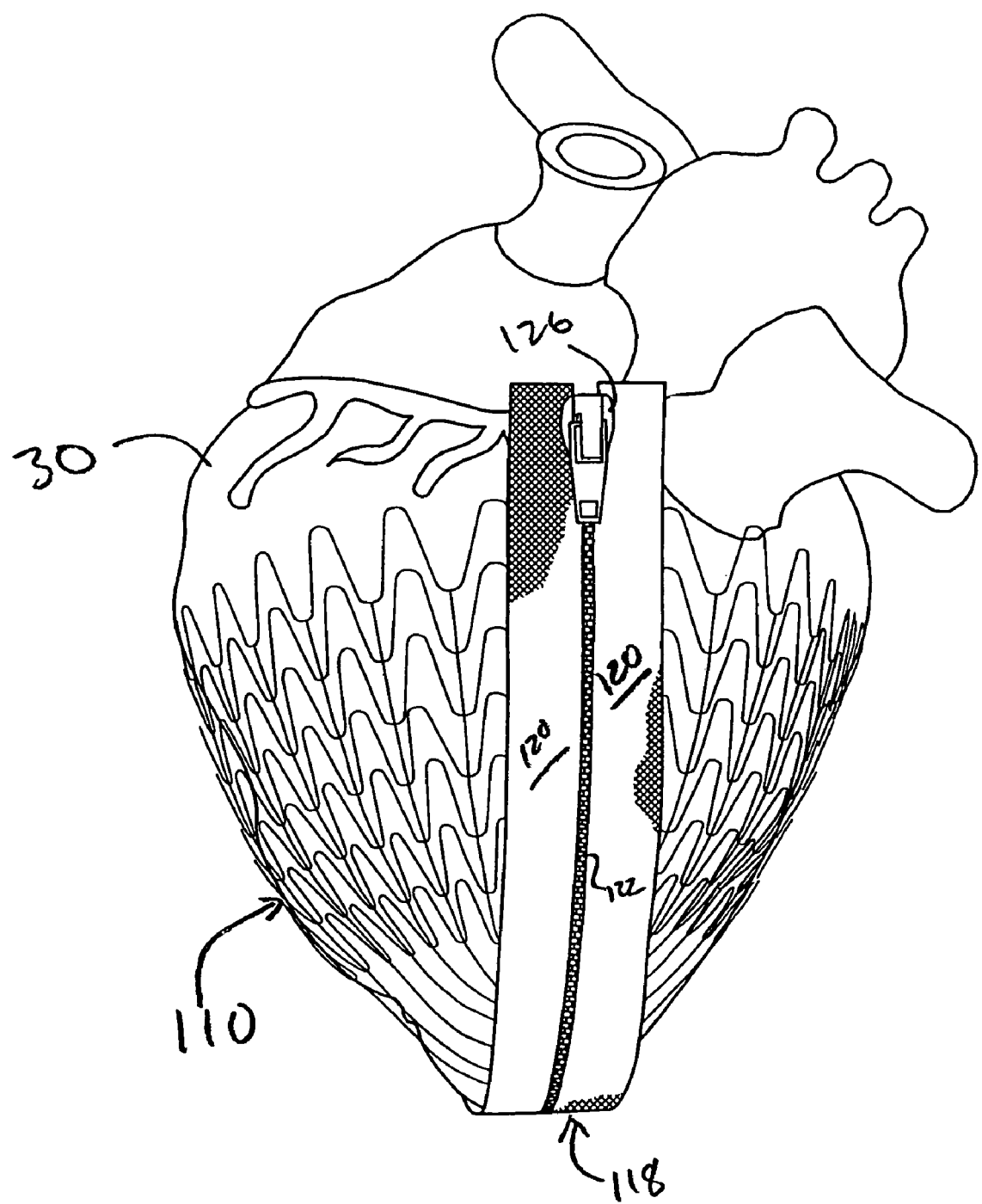
FIG. 12 shows the cardiac harness of FIG. 10 tightened around the heart.
Figure 13:
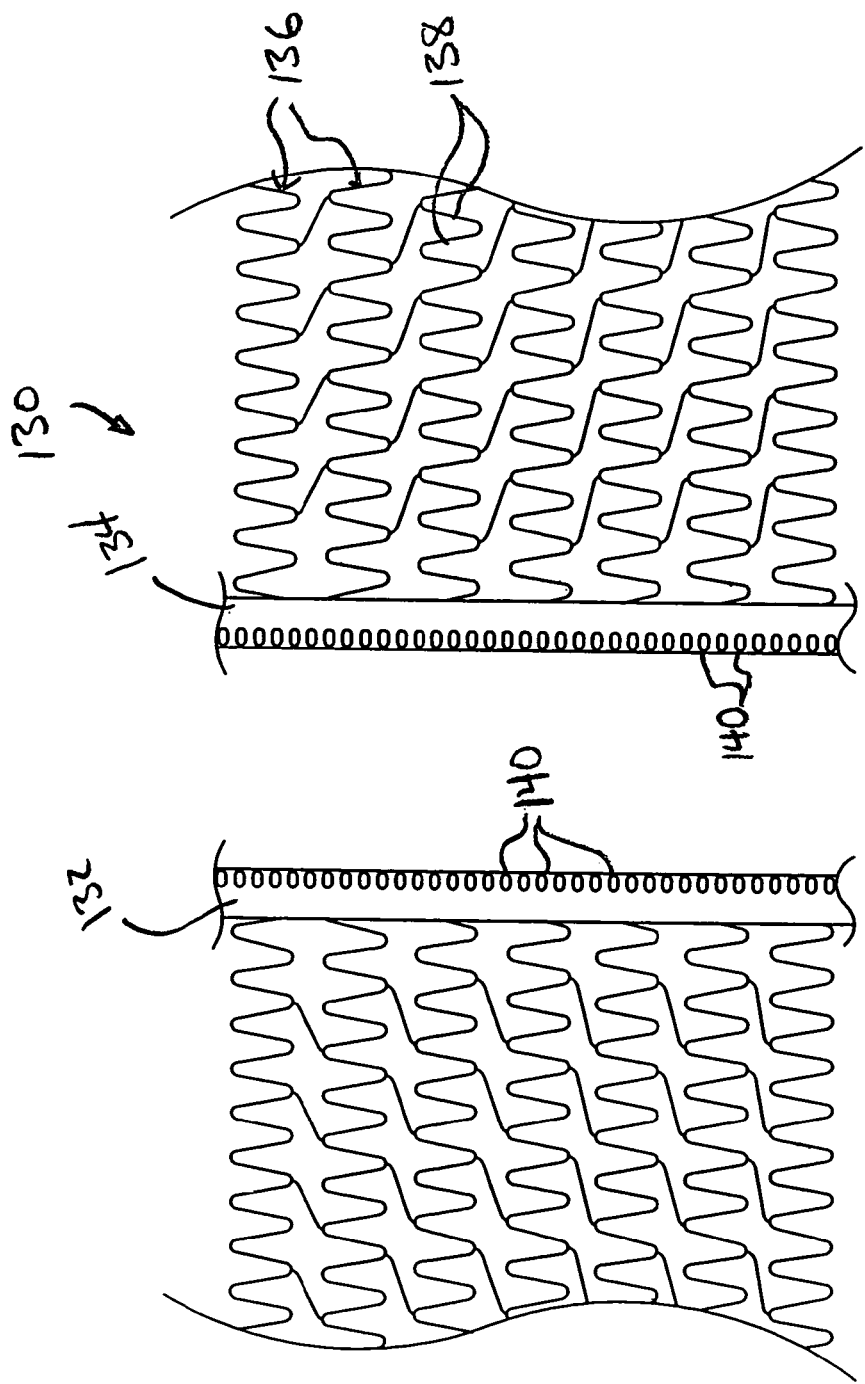
FIG. 13 shows two edge portions of an embodiment of a cardiac harness disposed adjacent one another.
Figure 14:
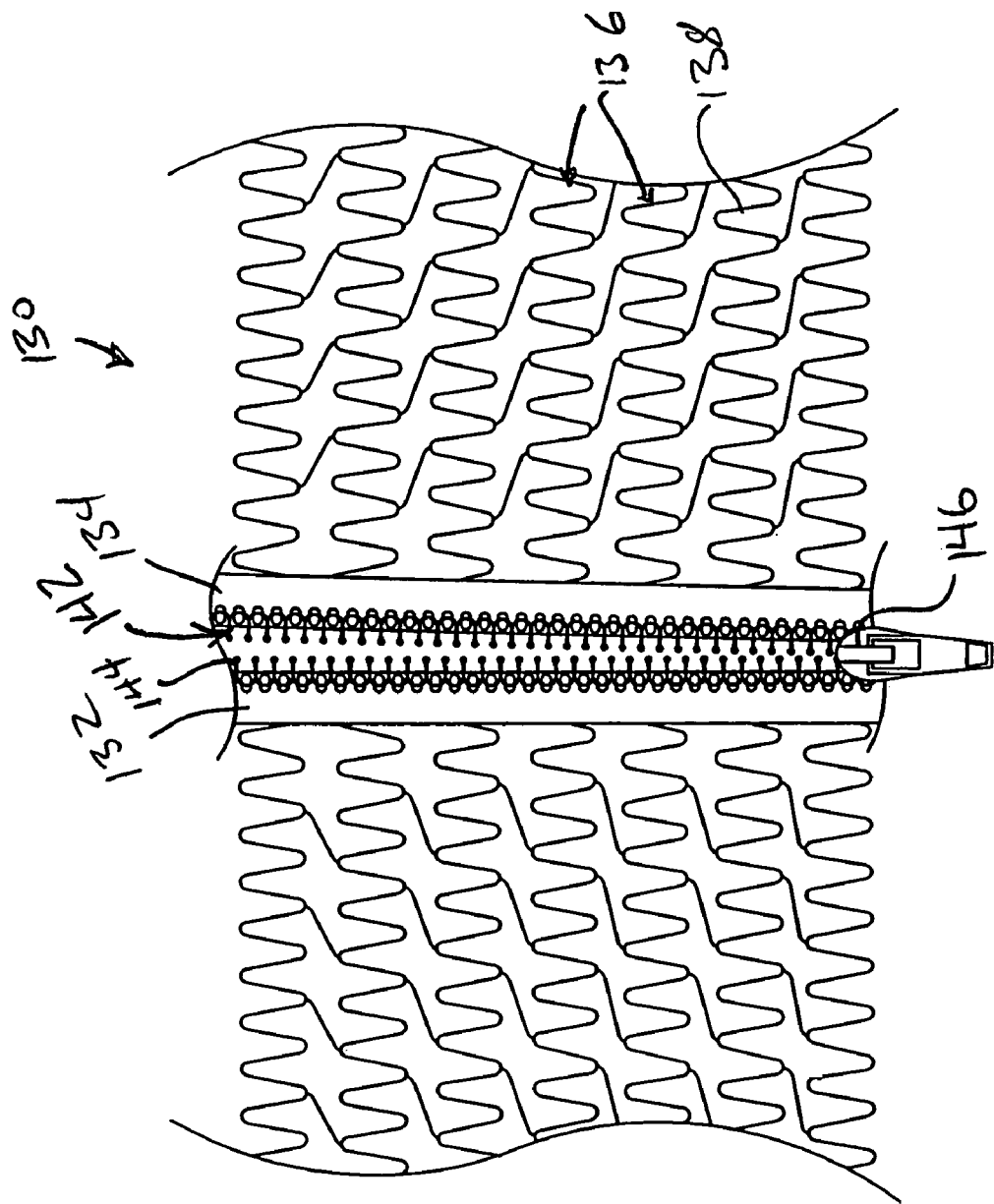
FIG. 14 shows the two edge portions of FIG. 13 with a zipper coupling attached to each edge portion.

With reference next to FIGS. 10-12, another embodiment of a cardiac harness 110 comprises opposing first and second longitudinal edges 112, 114. When the first and second longitudinal edges 112, 114 are aligned with one another, the harness 110 is substantially circumferentially continuous and is shaped to fit about a heart. A closure device 116 is attached along the first and second edges 112, 114. In the illustrated embodiment, the closure device 116 comprises a zip coupler 118 in the form of a zipper 119. Mating components 120 comprising zipper teeth 122 are disposed on a fabric backing 124 that is attached to the corresponding harness edge by sutures.

FIGS. 10-12 illustrate the harness 110 being installed over a patient's heart 30. To install the harness, the zipper 119 is disengaged and the harness 110 is fitted loosely about the heart 30 as shown in FIG. 10. The harness 110 does not fit circumferentially all the way around the heart when the spring hinges 125 are at rest. As a zipper actuator 126 or coupling member is advanced longitudinally along the mating components 120, as shown progressively in FIGS. 11 and 12, the mating components 120 interlock with one another so that the harness 110 is closed about the heart 30. The first and second edges 112, 114 of the cardiac harness 110 are drawn toward each other and held in position. In this manner, it is easy and effective to close the harness over the heart so as to circumferentially surround the heart, even though a resting size of the harness is smaller than the heart.

The actuator or coupling member 126 can be advanced by hand or can be held with a tool to advance it along the length of the mating components 120. Once interlocked, the mating teeth 122 provide circumferential strength for the harness 110 and also provide some longitudinal strength. When the harness is closed, the zip coupler 118 is interposed between the harness edges 112, 114, and the edges may thus be spaced from each other. However, circumferential forces in the harness 110 are communicated to spring hinges 125 adjacent the edges 112, 114 through the zip coupler 118.

It is to be understood that variations and embodiments of a zip coupler can be advantageously employed in the present invention. For example, any of a variety of zip coupling mechanisms can be used to obtain an effect similar to the illustrated zipper, which effect is that opposing edges are drawn transversely toward each other as an actuator member is moved longitudinally along the edges. Other exemplary zip coupling mechanisms include "zip-lock" type mechanisms in which a first elongate mating component having a male member engages a second elongate mating component having a female member.

In the illustrated embodiment, the coupling member 126 selectively locks or unlocks the mating components 120. Thus, if the coupling member 126 is advanced to close the harness 110 about the heart 30, but the clinician is not satisfied with the fit or positioning of the device, the coupling member 126 can be retracted so as to unlock the mating components and loosen the harness. This enables the clinician to easily adjust and resecure the device on the patient's heart.

After the mating components 120 have been locked together, the coupling member 126 can be left in place or can be completely removed from the zip coupling mechanism 118. The mating components 120 will remain interlocked after the coupling member 126 is removed. However, with a conventional zipper, when the coupling member has been removed, there is a chance that the mating components will unlock from each other if the ends of the components are not held together. To counteract this possibility, a secondary coupling 128 is provided to hold the mating components 120 in an interlocked position at two or more locations along their length. The secondary coupling 128 prevents the mating components from working apart from each other.

Secondary coupling members can comprise clips, sutures or the like. In another embodiment, the secondary coupling members comprise a pair of relatively small and biologically inert magnets arranged to hold the mating components together. The magnets preferably comprise rare earth magnets made of neodymium, iron and/or boron and are available from Jobmaster Magnets. In one embodiment, the magnets are attached to the edges of the cardiac harness or to the mating components by an epoxy, and are arranged to automatically engage one another when the harness is closed. As such, no additional steps are required to apply a secondary coupling.

The mating components 120 and coupling member 126 can be formed of any material, such as metals or polymers. As discussed above, the mating components 120 may be attached to a fabric backing 124, which in turn is attached to the corresponding harness edge 112, 114. However, it is to be understood that the elongate mating components can also be attached directly to the harness, or can even be co-formed therewith.

Figure 15:
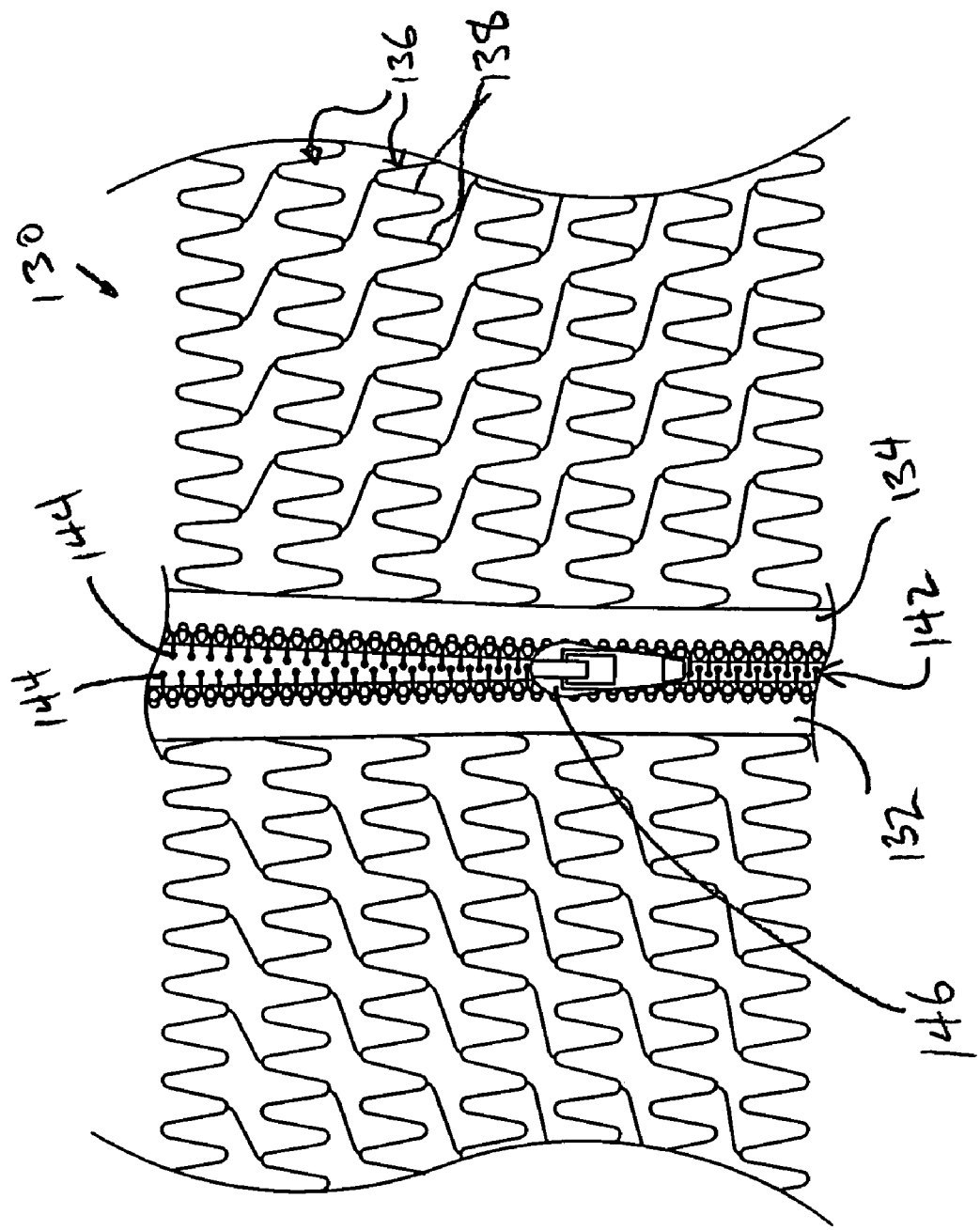
FIG. 15 shows the edge portions of FIG. 14 partially coupled to one another.
Figure 16:
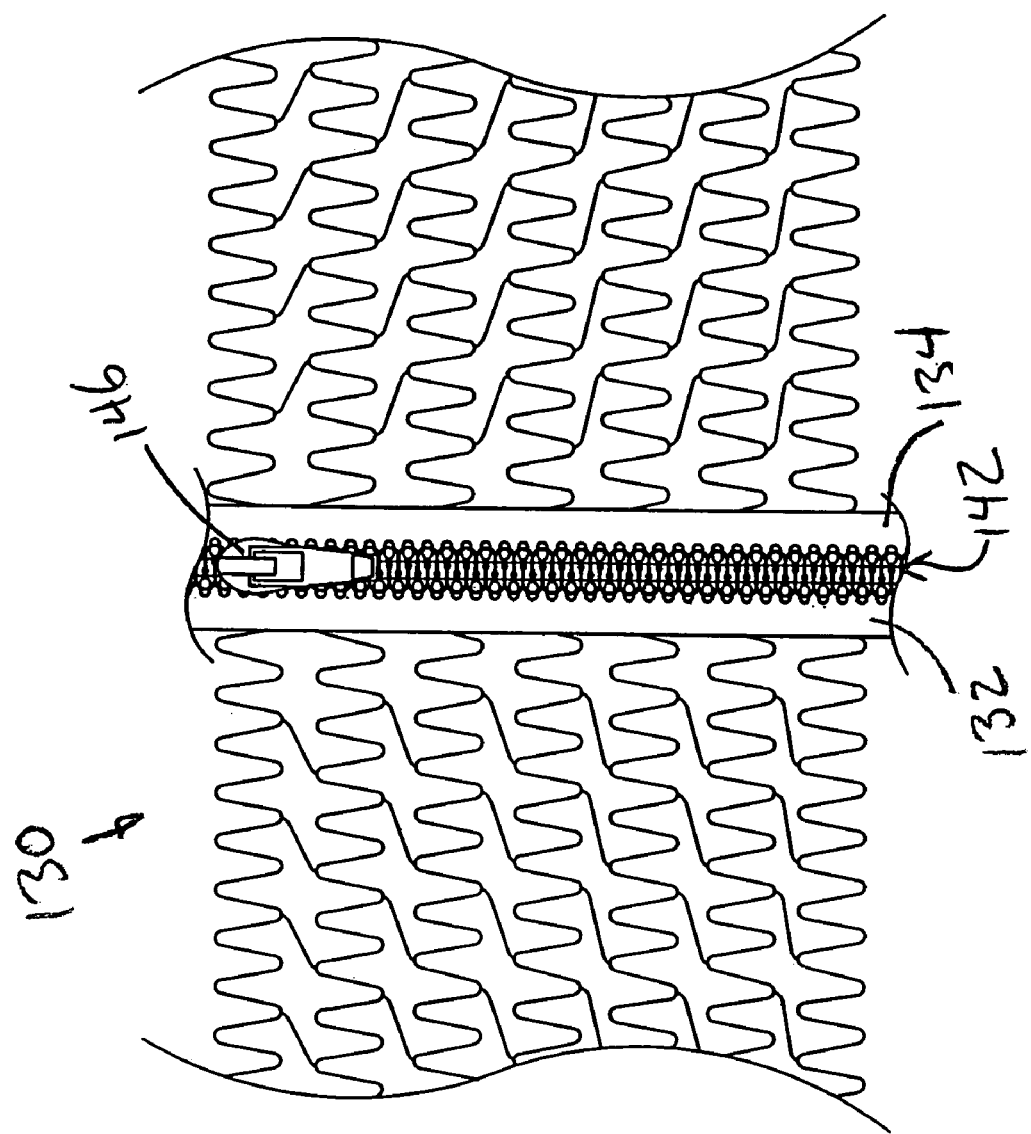
FIG. 16 shows the edge portions of FIG. 14 more fully coupled to one another.

FIGS. 13-16 illustrate an embodiment in which elongate mating components are attached directly to edges of a cardiac harness. With specific reference to FIG. 13, a portion of an etched cardiac harness 130 is shown. The etched harness 130 includes a first longitudinal edge 132 and a second longitudinal edge 134. Each edge 132, 134 connects to several rows 136 of interconnected springs 138. A series of small holes 140 are provided along each longitudinal edge 132, 134. As shown specifically in FIG. 14, an elongate mating component 142 is attached along each edge. In the illustrated embodiment, the mating components 142 comprise zipper teeth 144 that are attached to the edges 132, 134 by sutures, adhesives or like which extend through the holes 140. FIGS. 15 and 16 show an actuator or coupling member 146 being advanced along the mating components 142 so as to draw the adjacent edges 132, 134 together in an interlocked fashion.

In the illustrated embodiment, a zip coupling mechanism is used in conjunction with a cardiac harness 130 having spring hinges 138. It is to be understood, however, that a zip coupling mechanism can be used with any type of cardiac harness. For example, a cardiac harness constructed of an elastic or non-elastic woven or knit fabric, polyester mesh or other material can include a zip coupling mechanism. Such a harness can have first and second edges having elongate mating components that can be coupled together by a coupler member in a manner as discussed above.

The mating components can be attached directly to the first and second edges, or can be mounted on a fabric backing which is attached to the edges. In some embodiments, the fabric backing comprises a compliant or elastic material. As such, even if the harness is relatively inelastic, the elastic fabric backing of the zip coupler provides some compliance. As such, there is less of a chance that the harness will be too tight when installed on the heart.

An important step in using a zip coupling apparatus is engaging the coupling member 126, 146 with both of the elongate mating members 120, 142 so that the mating members will interlock appropriately with each other as the coupling member is advanced. In an additional embodiment, a harness has a zip coupling mechanism having elongate mating members that are substantially longer than the harness so that beating of the heart does not substantially disturb a connection end of the mating members at which the coupling member is installed. In a still further embodiment, the mating members extend out of a patient's body cavity when the harness is placed adjacent to the heart and is ready to be finally coupled thereto. In this manner, the clinician can engage the coupling member with both elongate mating components at a position outside of the patient's body. Such engagement thus is comparatively easy. The clinician then advances the coupling member so as to close the harness about the heart. In another embodiment, the coupling member is already engaged with the elongate mating components when the harness is advanced into the patient's body cavity.

Once the coupling member is engaged, it can be advanced along the elongate mating components until the mating components are locked together. The coupling member can continue to be advanced until it extends. off of the mating components, and the coupling member can then be removed from the patient's body. The elongate mating components can then be trimmed so that they extend along the harness edges and have relatively little surplus length. As discussed above, magnets or other secondary coupling members can be provided to prevent the mating components from unraveling.

Modular Construction

In accordance with another embodiment, a cardiac harness includes a plurality of individual components or modules that are assembled together to form a cardiac harness. The modules can include zip couplings so that assembly of the harness comprises using the zip couplings to engage adjacent modules with each other. Other methods and apparatus for coupling adjacent modules, such as applying clips, glue or the like, can also be used. Still further, edges of at least some of the modules can be manufactured so as to engage opposing edges of adjacent modules through hooks, compression fittings or the like.

Figure 17:
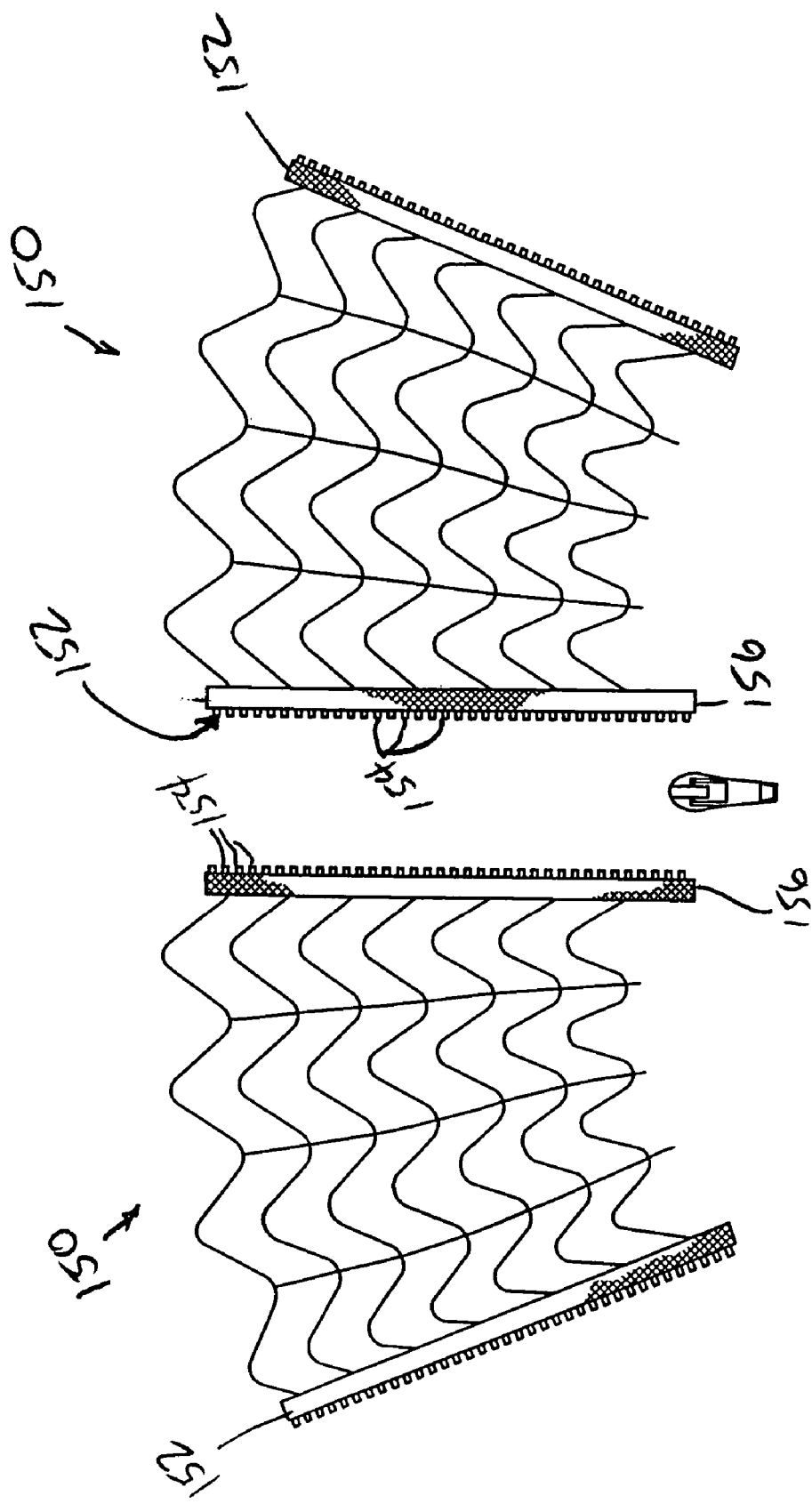
FIG. 17 illustrates adjacent modules of a cardiac harness prior to being connected to one another according to one embodiment.
Figure 18:
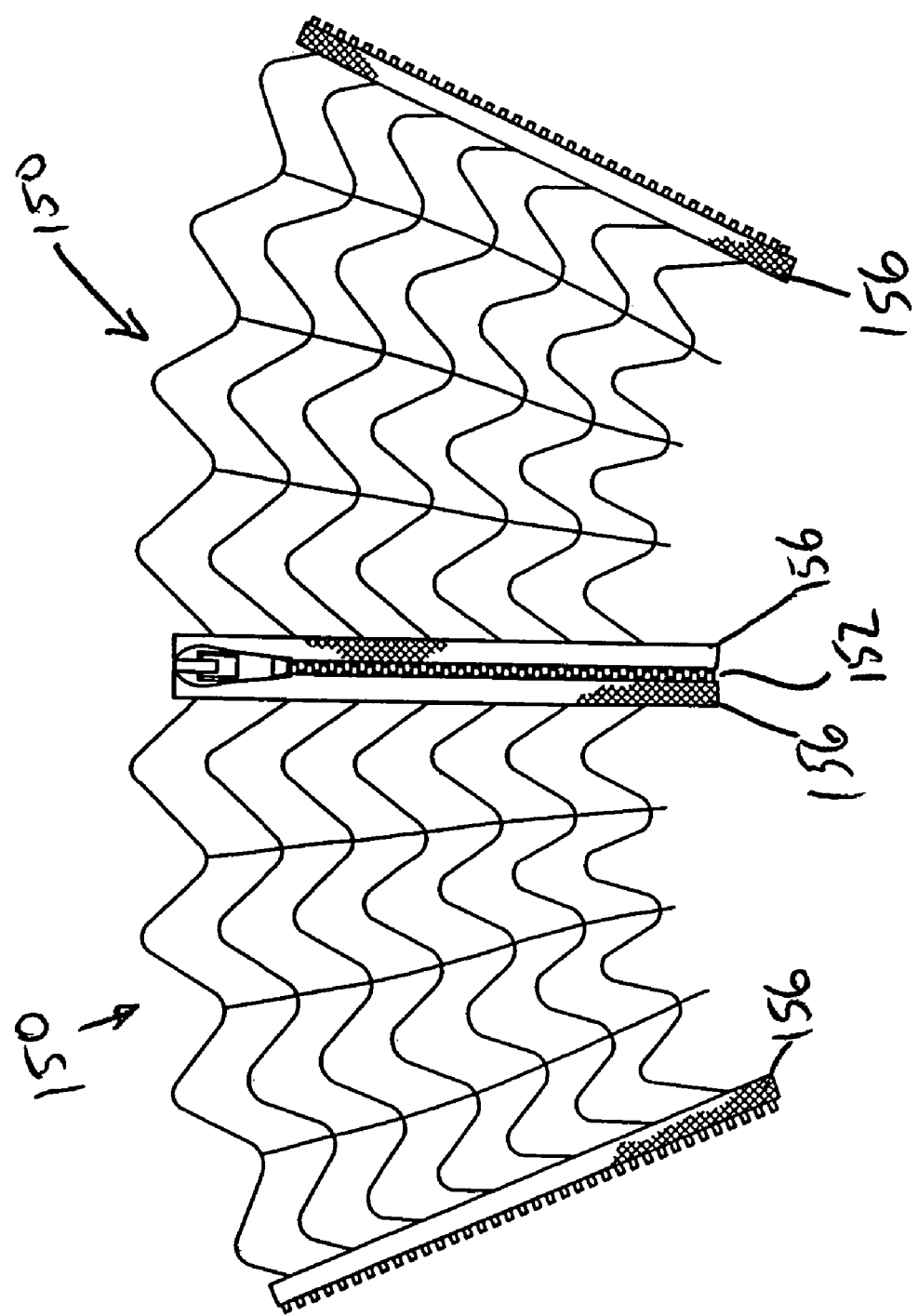
FIG. 18 shows the modules of FIG. 17 connected to one another.

With reference next to FIGS. 17 and 18, modules 150 of an embodiment of a cardiac harness are shown. Each of the modules 150 has an elongate mating member 152 comprising zipper teeth 154 attached to an edge 156 of the corresponding module 150. The mating members 152 are coupled together in a manner as discussed above. As shown in FIG. 18, multiple modules 150 are joined to one another by engaging the mating members 152. Successive modules 150 can be added until a full cardiac harness is formed.

Figure 19:
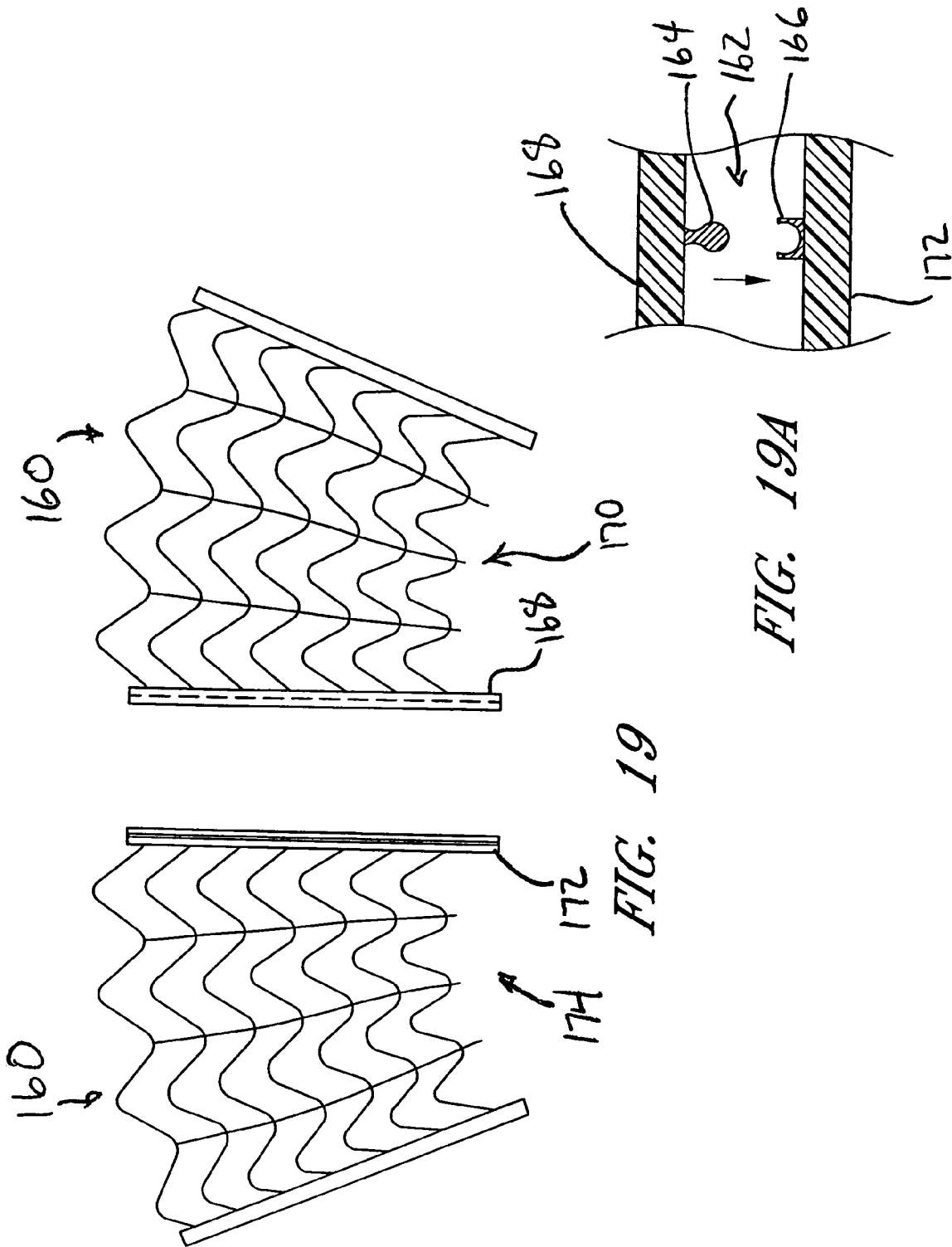
FIG. 19 shows adjacent modules of a cardiac harness configured to be connected to one another according to another embodiment.
Figure 20:
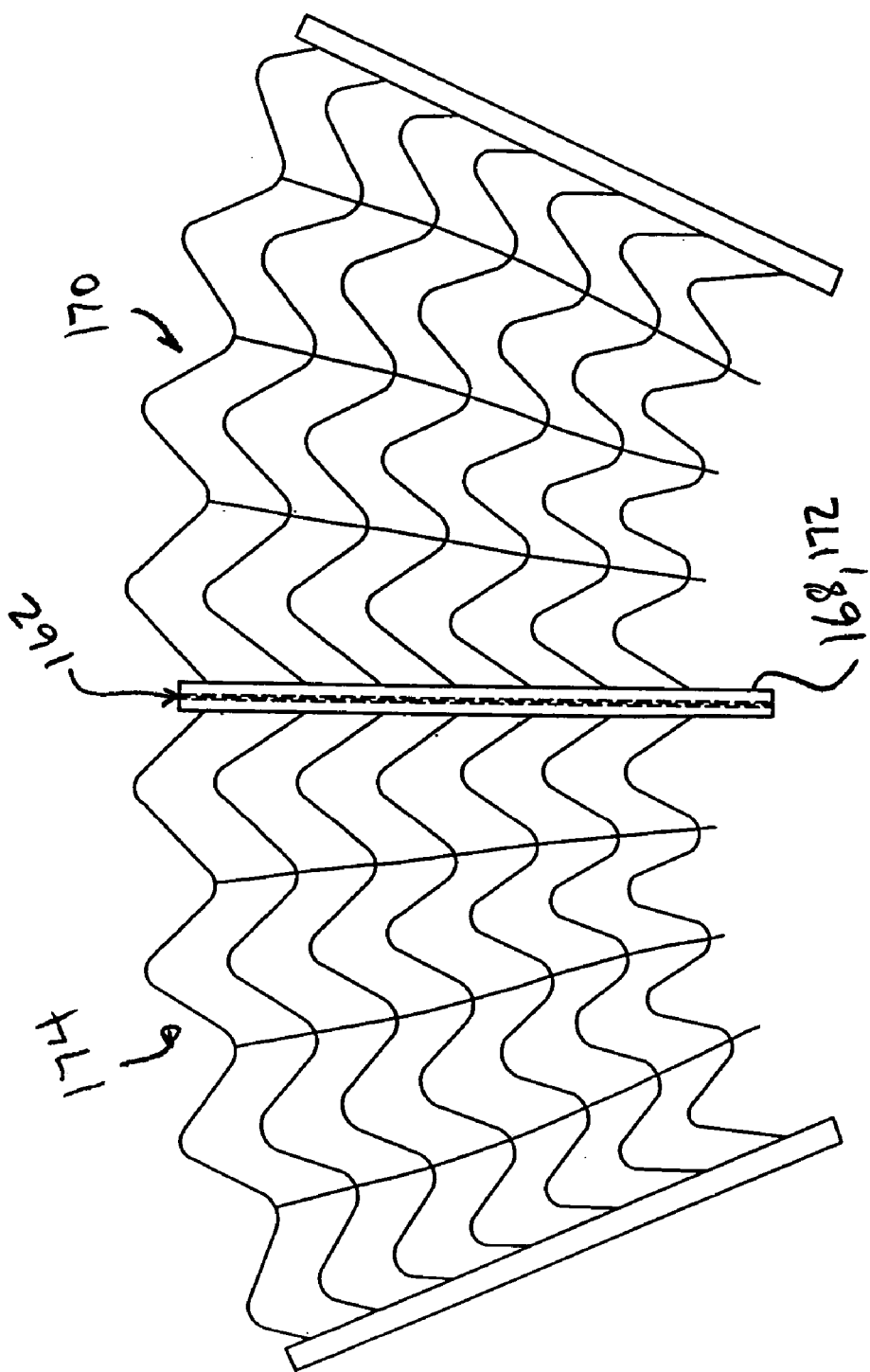
FIG. 20 shows the modules of FIG. 19 connected to one another.

FIGS. 19, 19*a* and 20 show another embodiment of cardiac harness modules 160 comprising a zip coupler 162 in the form of a "zip lock" fastener which comprises a male member 164 adapted to engage a female member 166. The male member 164 is mounted along an edge 168 of a first module 170 and the female member 166 is aligned along an edge 172 of a second module 174. When the male and female members 164, 166 are engaged, the modules 170, 174 are held together as shown in FIG. 20. In the embodiments illustrated in FIGS. 17-20, the respective zip couplers 162 are interposed between adjacent modules 170, 174, and the module edges 168, 172 do not actually contact one another.

It is to be understood that several types of fasteners or coupling mechanisms can be used to couple adjacent modules. These mechanisms include releasable mechanisms such as the zip coupling mechanisms shown in FIGS. 17-20 and also include permanent coupling mechanisms. For example, in another embodiment, adjacent modules 150, 160 are connected to one another by applying a layer of silicone on and between the modules. Various polymers can also be used to permanently bond or couple adjacent modules to one another.

Assembly of cardiac harness modules can be accomplished ex vivo and/or in vivo. In vivo assembly can be performed as part of a minimally-invasive surgical delivery of the device. Modular construction of the harness is advantageous for minimally-invasive procedures because the profile of each module is smaller than the profile of the assembled harness. A smaller delivery opening and passage to the heart can be used if the harness is advanced module by module than if the harness is advanced fully assembled. Multiple zip couplings can be used to assemble the harness in vivo.

A modular harness allows for precise customization of the harness to a particular patient's heart size and needs. Compliance and placement of spring elements can be specially adapted for a patient's heart. For example, certain modules having a greater collective spring constant may be joined with modules having greater flexibility so that the stiffer spring elements are disposed around the patient's left ventricle, while the more compliant spring elements are provided around the rest of the patient's heart. Still further, some modules may include spring hinges while others do not.

A modular approach also allows a cardiac harness manufacturer to accommodate a broad range of heart shapes and sizes while maintaining a relatively low inventory of module sizes. This is because a limited number of modules of different sizes and compliance can be mixed and matched to construct cardiac harnesses having a broad range of sizes and compliance as required by patients.

The modules 150, 160 can be formed in various sizes and shapes. For example, the modules can comprise longitudinal strips, circumferential strips, spiral strips, or the like.

Scrolled Harness

With reference next to FIGS. 21-24, another embodiment of a cardiac harness 180 and a method for installing the harness is provided and illustrated. With specific reference to FIG. 16, the illustrated cardiac harness 180 comprises a plurality of rows 182 of undulations comprising spring hinges 184. As can be seen in the figure, the construction shares many similarities with other embodiments such as those described in FIGS. 3 and 7; however, the illustrated harness 180 is generally ribbon- or fan-shaped and has first and second ends 186, 188. In the illustrated embodiment, the ribbon-shaped harness 180 is generally rectangular. In other embodiments, the ribbon-shaped harness 180 can be generally arcuate.

As with previously discussed harness embodiments, the ribbon-shaped harness 180 preferably is formed of a flexible material. In the illustrated embodiment, the ribbon-shaped harness is etched from a flat sheet of Nitinol. In other embodiments, other materials, such as drawn Nitinol wire, can be used to formed a ribbon-shaped harness. Additionally, such a harness could be constructed out of flexible, non-metal and non-superelastic materials.

Figure 21:
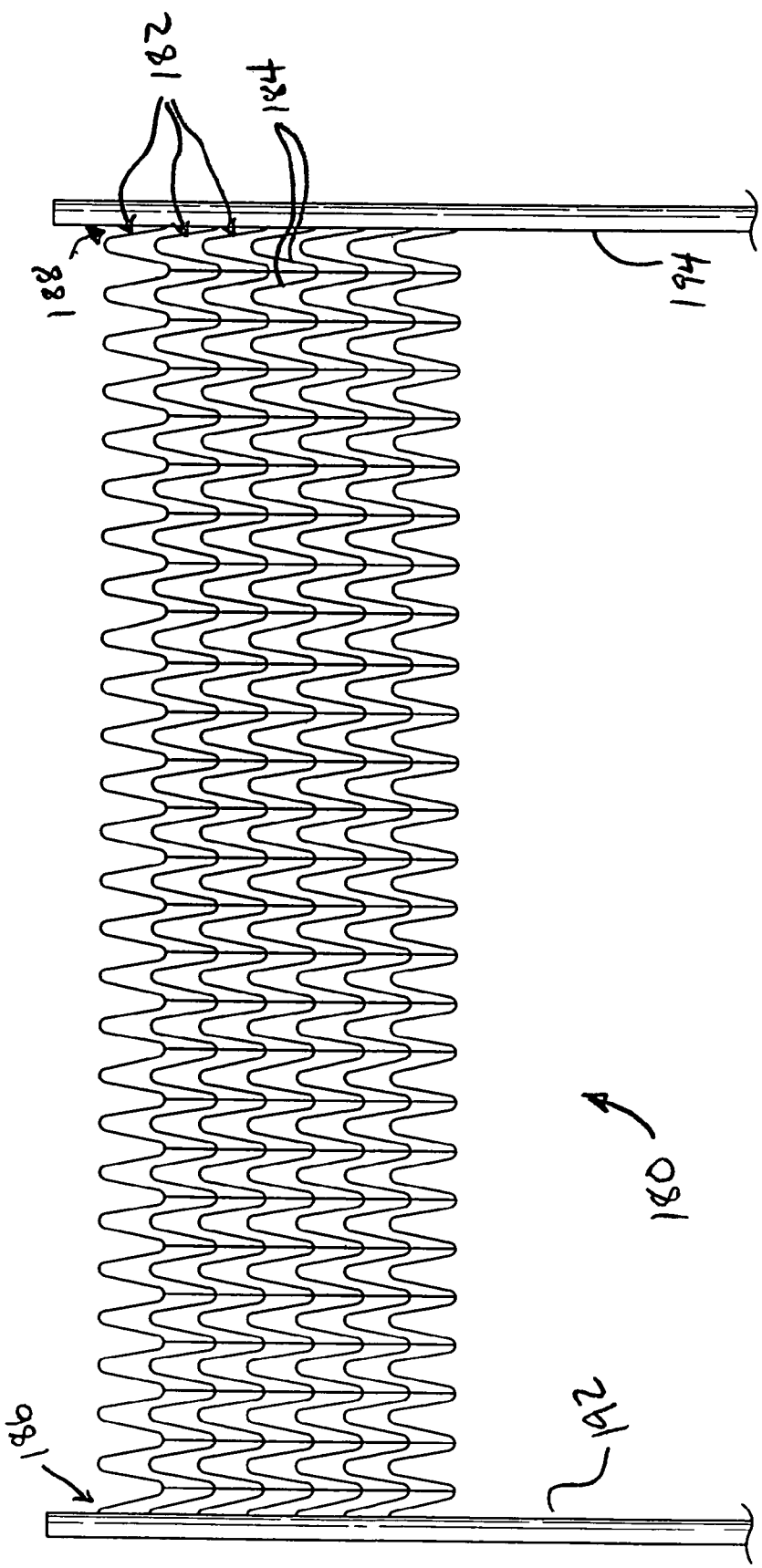
FIG. 21 shows an embodiment of a ribbon-shaped harness connected to deployment rods.

A deployment apparatus 190 comprises first and second deployment rods 192, 194 which are depicted in FIG. 21. The first and second ends 186, 188 of the cardiac harness 180 are connected to the deployment rods 192, 194. The substantially flat, fan-shaped configuration of the harness 180 allows a clinician to place the harness adjacent the heart 30 and, using the rods 192, 194, to easily and quickly wrap the harness 180 around the heart 30 (See FIG. 22), even when the heart is beating. This construction and mode of deployment allows the harness to be installed without having to be slid longitudinally over the heart epicardium. Trauma to the epicardium is minimized or avoided.

Figure 23:
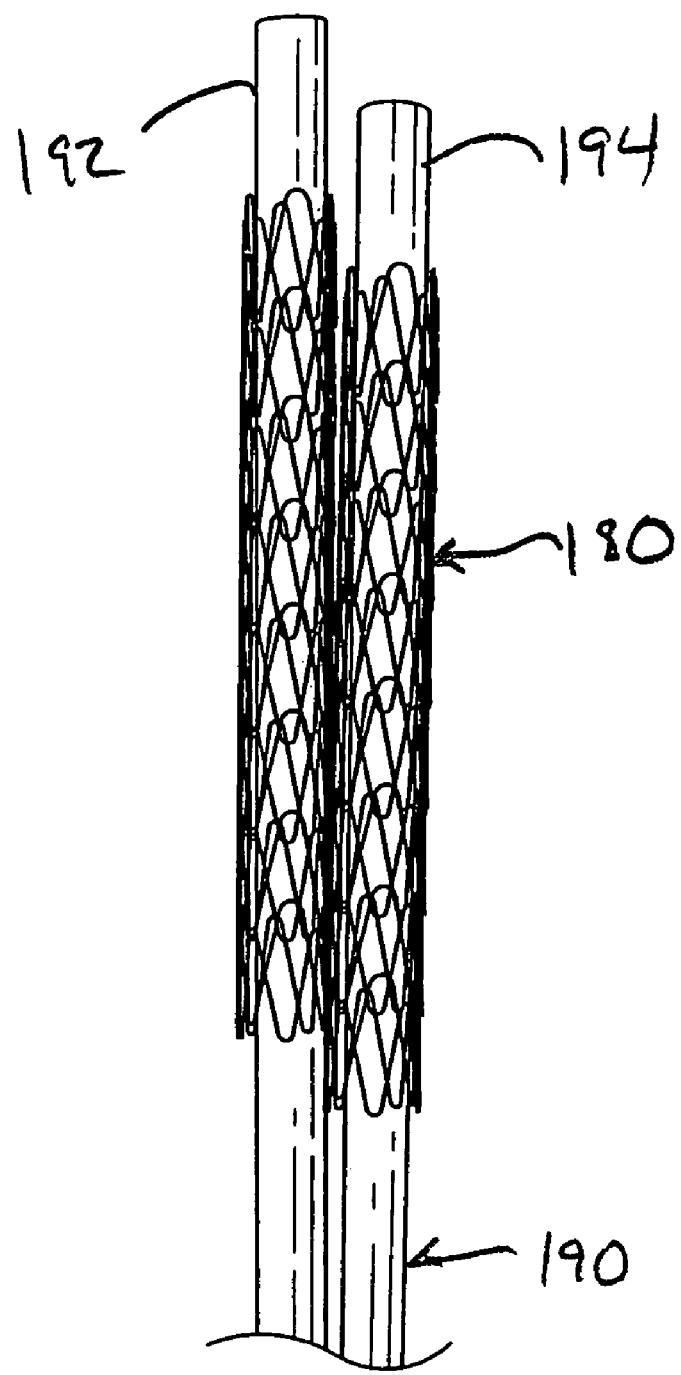
FIG. 23 shows the harness of FIG. 21 wrapped in a scroll manner about the deployment rods.

With reference next to FIG. 23, the harness 180 preferably is wrapped about the deployment rods 192, 194 in a scroll-type configuration prior to deployment onto the heart. The scroll-type configuration has a very low profile and can be inserted into a patient's body cavity using minimally-invasive surgical methods.

Figure 22:
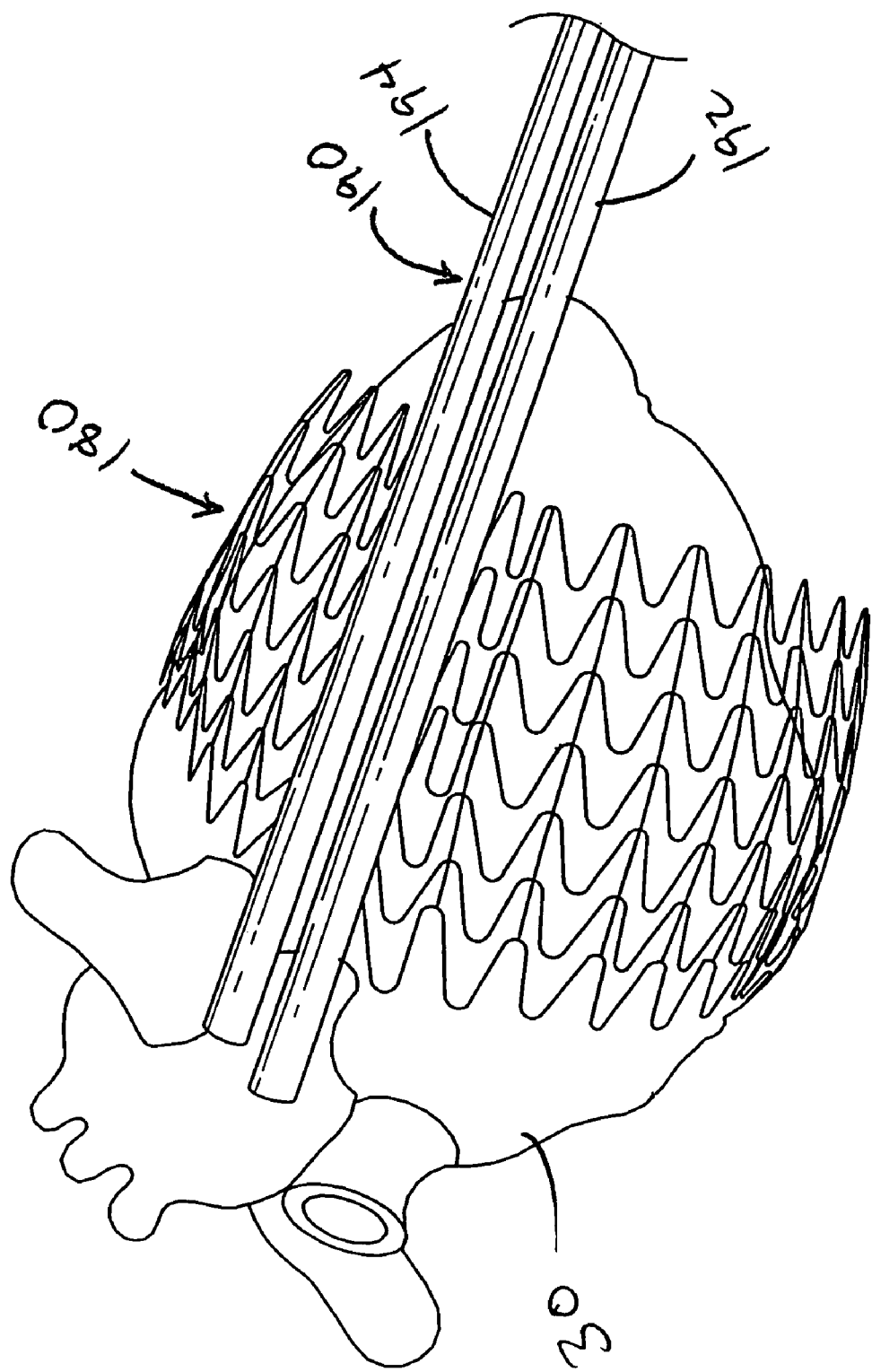
FIG. 22 shows the harness of FIG. 21 wrapped around a heart.
Figure 24:
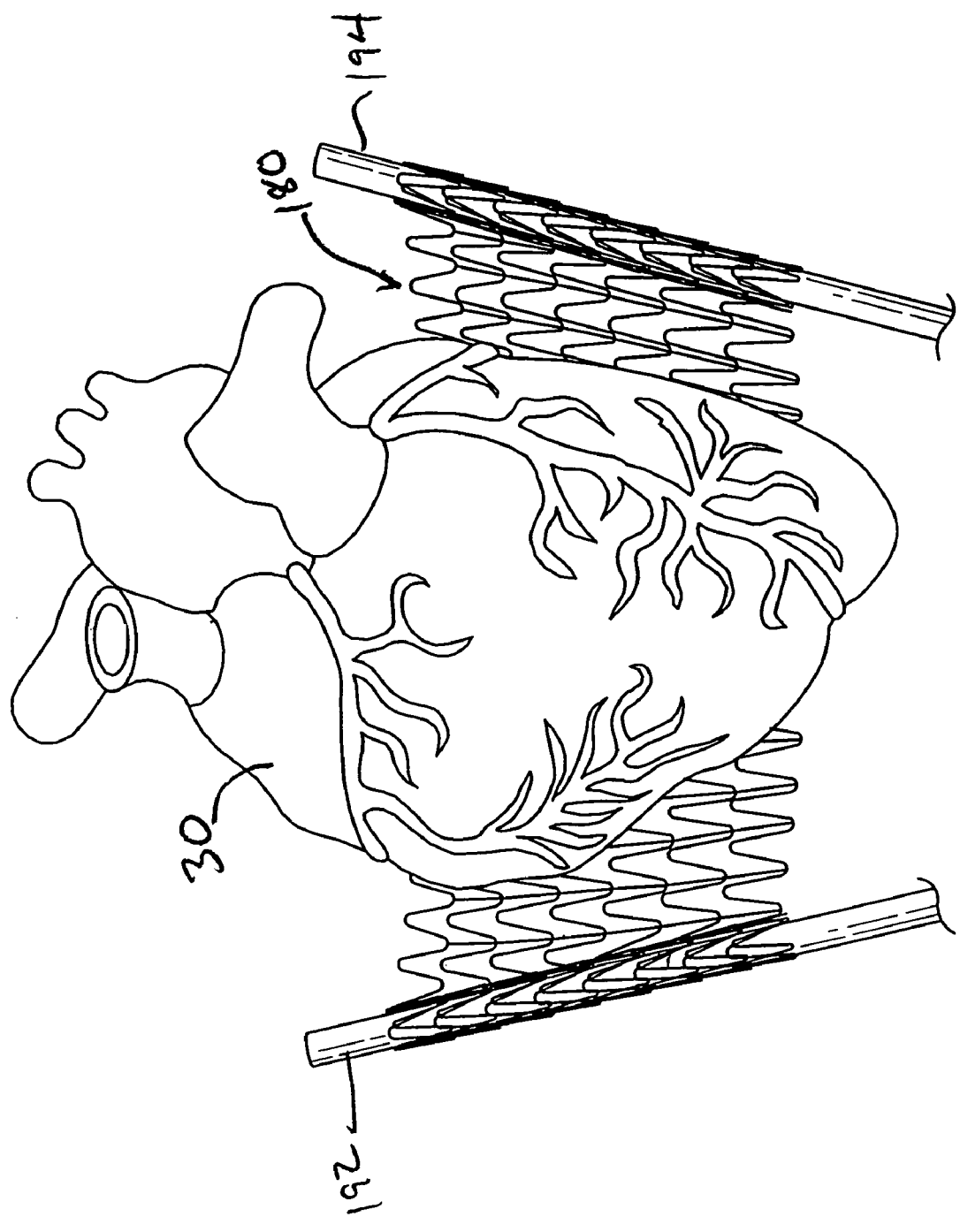
FIG. 24 shows the harness of FIG. 21 partially deployed on a heart.

To install the harness 180 on the patient's heart 30, the clinician positions the rods 192, 194 having the harness scrolled thereupon immediately adjacent the heart's epicardium, and then moves the rods 192, 194 around opposing sides of the heart while rotating the rods. As the rods move about the heart, the harness 180 unscrolls from the rods and onto the heart epicardium, as illustrated in FIGS. 22 and 24. Once the harness 180 completely encircles the heart, as shown in FIG. 22, the first and second ends 186, 188 of the harness 180 are engaged with one another. The ends are then released from the rods 192, 194 and the rods are removed. The harness 180 is left in place on the patient's heart 30.

Any suitable apparatus or method can be used to engage the ends with one another and/or to releasably hold the ends to the deployment rods. For example, clips, sutures, surgical adhesives, magnets, biodegradable materials, etc. can suitably be used.

Figure 25:
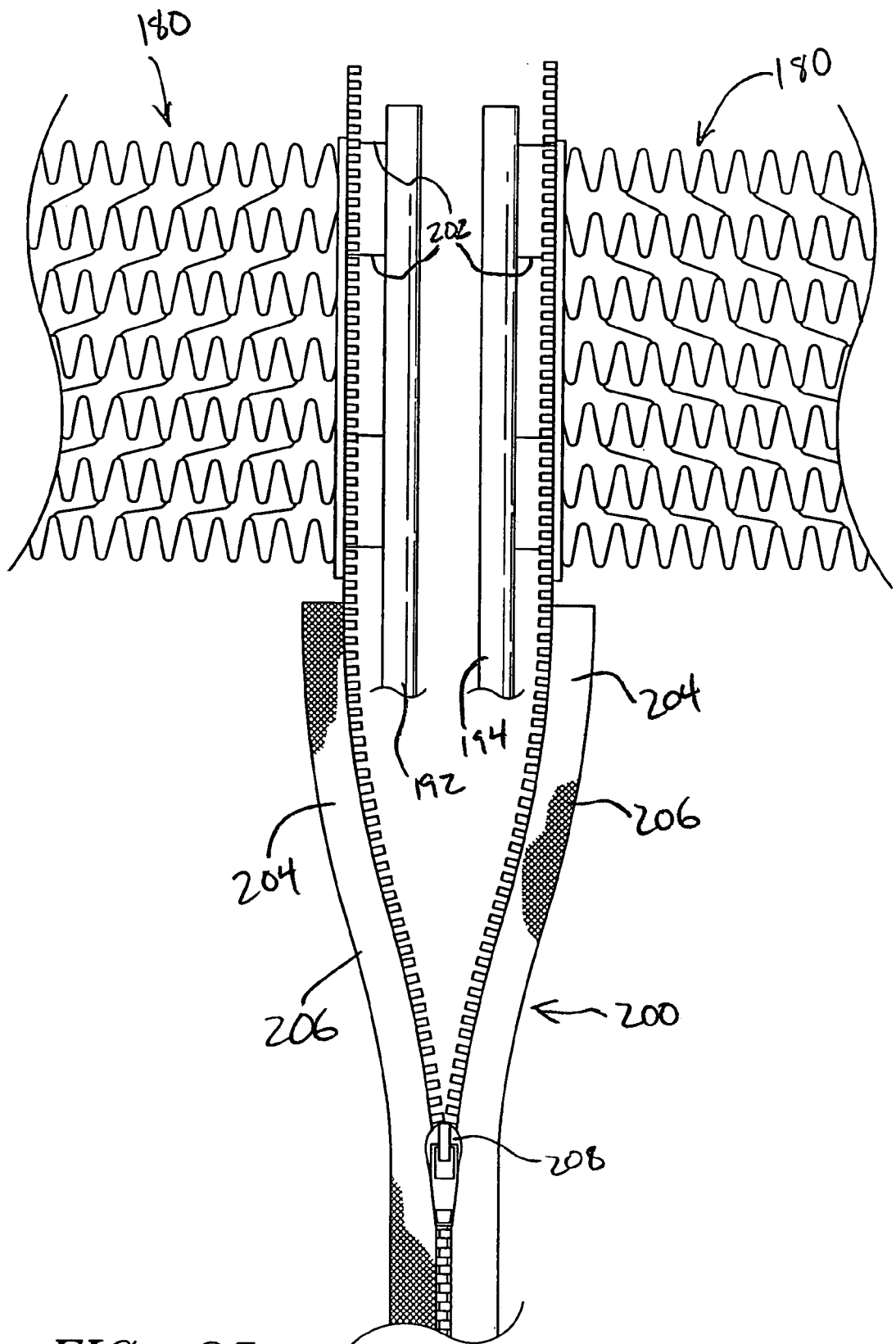
FIG. 25 shows an embodiment of a ribbon-type harness with the first and second edges of the harness about to be joined together.

With next reference to FIG. 25, one embodiment of a ribbon-type harness 180 employs a zip coupling mechanism 200 to aid closure of the harness. Connecting members 202 extending from the ends of the harness 180 connect the harness to the rods 192, 194. In the illustrated embodiment, the connecting members 202 comprise suture material. Elongate mating members 204 are provided along the first and second ends 186, 188 of the fan-shaped cardiac harness 180. The elongate mating members 204 extend far beyond the ends 186, 188 so as to extend out of the patient's body cavity during surgery. Preferably, a portion of the mating members 204 is connected directly to the ends 186, 188 and a fabric backing 206 or the like is provided to support the mating members 204 proximal of the harness ends.

Once the harness 180 is placed around the heart 30 as depicted in FIGS. 22 and 25, the clinician advances a coupling member 208 of the zip coupling mechanism 200 along the elongate mating members 204 into the body cavity and along the harness. As the coupling member 208 moves along the mating members 204 on the harness 180, the connecting members 202 are detached from the deployment rods 192, 194, and the rods are moved out of the way. The coupling member 208 draws the first and second ends 186, 188 of the harness matingly adjacent each other, thus holding the harness 180 in place on the patient's heart 30. Once the coupling member 208 has been fully extended, extra and unnecessary portions of the mating members 204 are trimmed away and one or more secondary connector members can be attached to prevent the interlocked mating members from unraveling.

It is to be understood that a variety of methods and apparatus for joining the opposing edges of the harness can be employed. For example, magnets, sutures, clips, medical adhesives and the like can be used to join the ends In one embodiment, a Nitinol ribbon-type harness is formed to fit a patient's heart size and shape and then is annealed in that position so that it will "remember" the shape. The harness will assume the annealed shape within a patient's body even though the harness may be deformed when scrolled upon the rods. In another embodiment, the Nitinol harness is first scrolled about the rods and then annealed in the scrolled configuration. For both of these embodiments, once the harness is deployed around the patient's heart, it exerts an inwardly-directed compressive force on the heart, which force will alleviate wall stress during diastolic filling of the heart.

Figure 26:
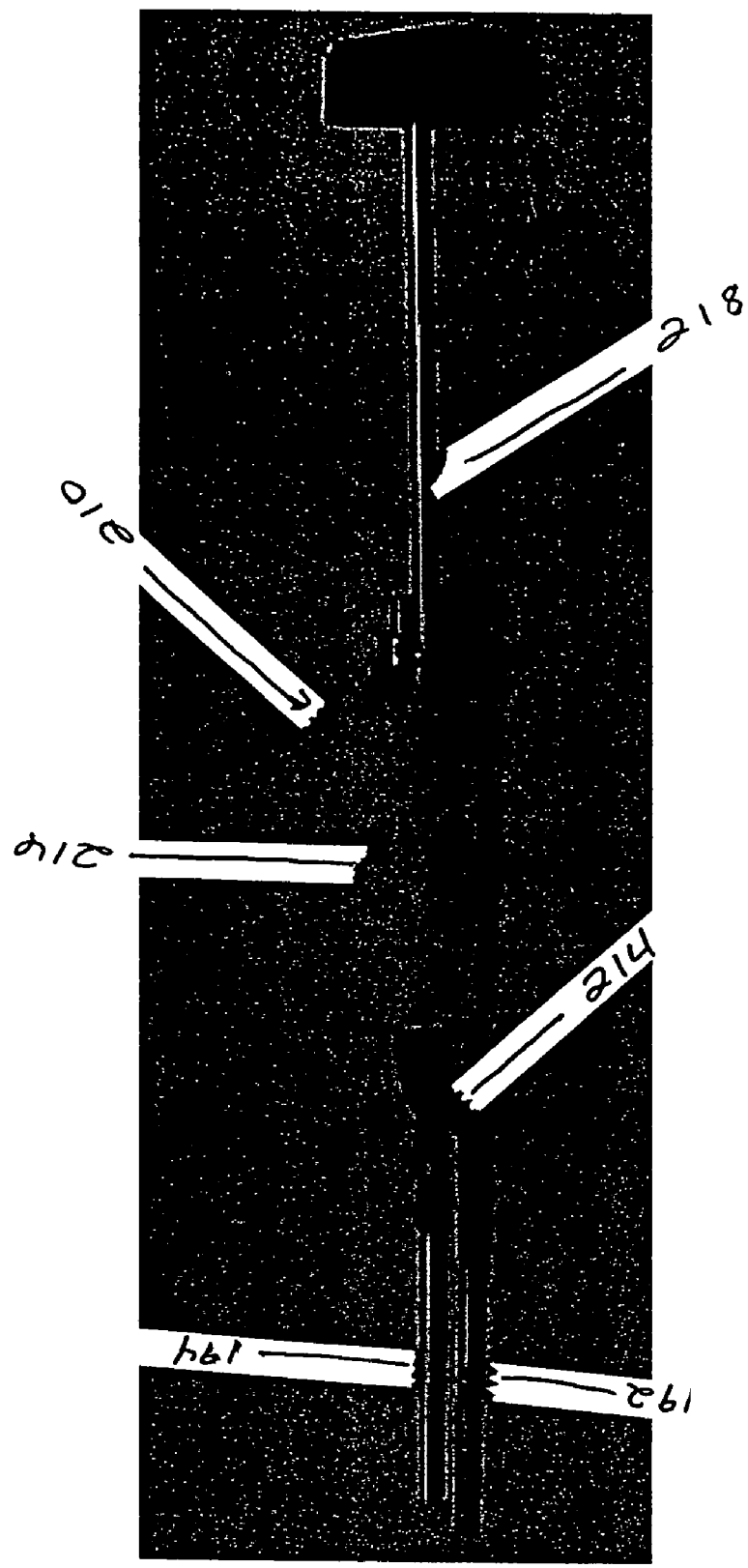
FIG. 26 shows a side view of a delivery apparatus for a ribbon-type harness.
Figure 27:
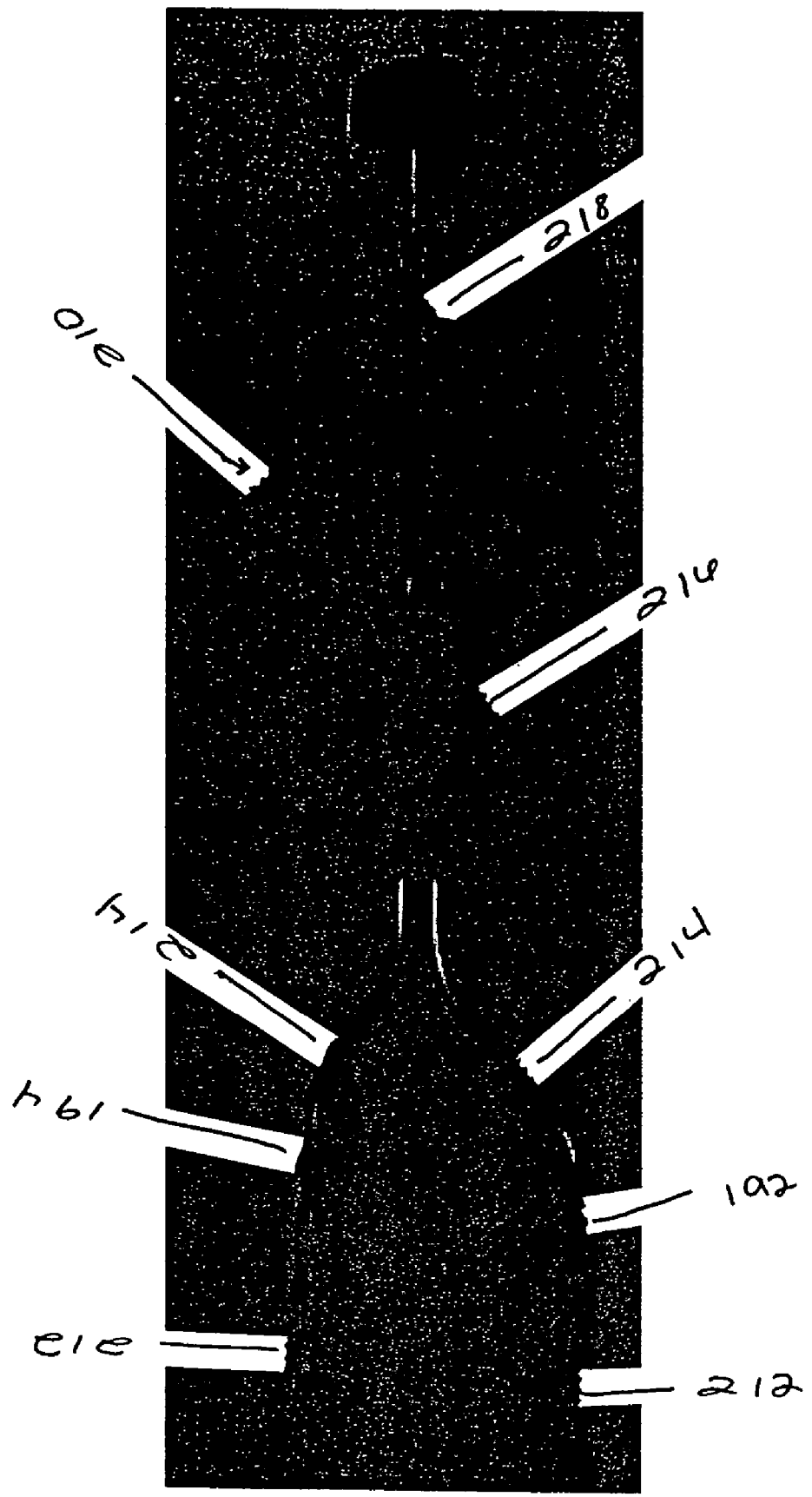
FIG. 27 illustrates another view of the delivery apparatus of FIG. 26.
Figure 28:
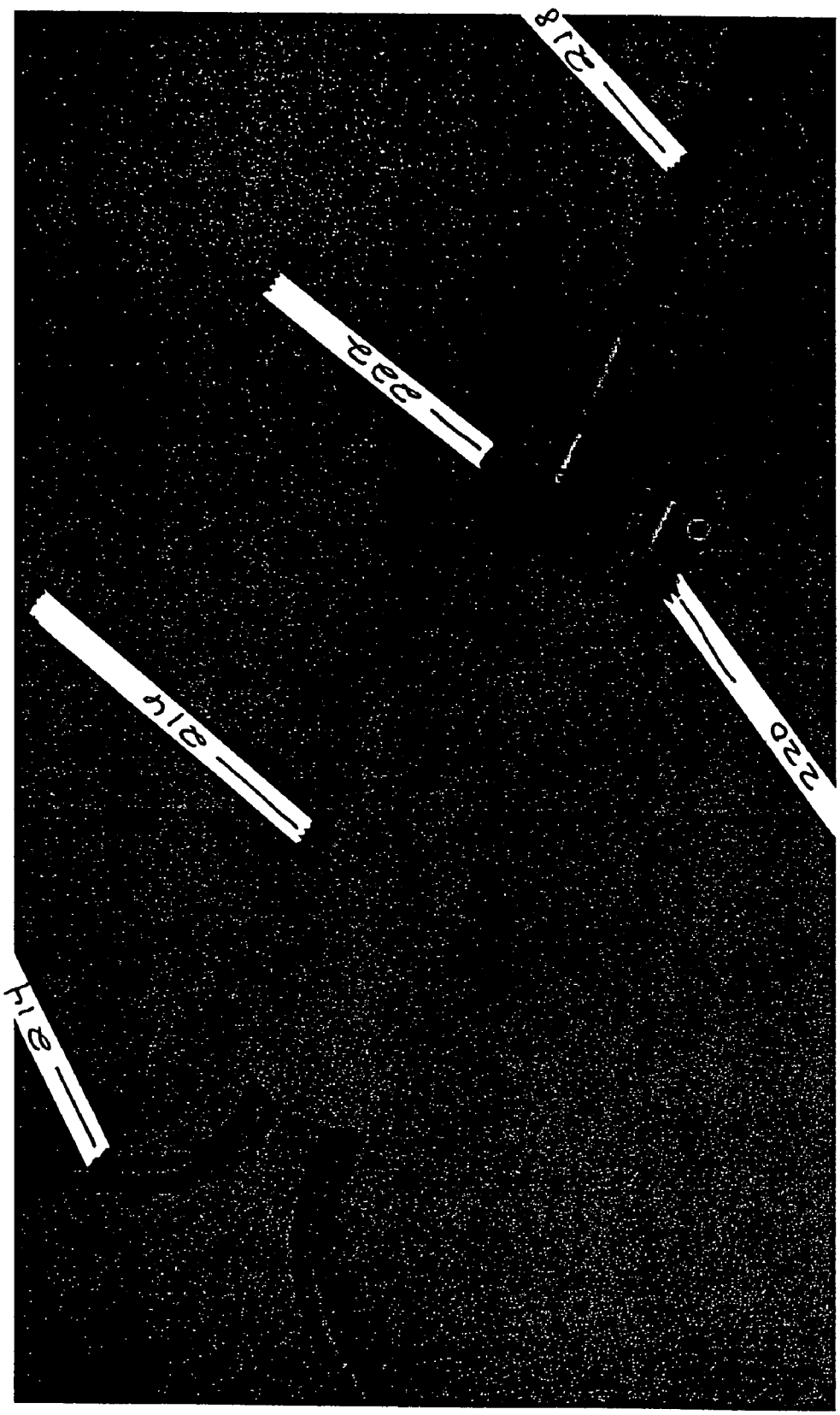
FIG. 28 shows a close-up view of a portion of the delivery apparatus of FIG. 26.

With reference next to FIGS. 26-28, a scroll harness delivery apparatus 210 is shown. The scroll harness delivery apparatus 210 includes first and second deployment rods 192, 194 that are adapted to hold the harness 180 in the scrolled configuration. The harness is attached to a holding portion 212 of each rod 192, 194 which is positioned adjacent a distal end of the corresponding rod. A bending portion 214 is provided on each rod 192, 194 proximal of the holding portion 212. As such, the rods are configured so that as they rotate in opposite directions relative to one another, the holding portions 212 of the adjacent rods 192, 194 move from being immediately next to one another (see FIG. 26) to being spaced apart (see FIG. 27). Upon still further rotation, the holders 212 again become disposed immediately next to one another.

A proximal end of the deployment rods 192, 194 is supported by a handle 216. An actuator rod 218 extends proximally from the handle 216. The actuator rod 218 rotates with the first deployment rod 192. With specific reference to FIG. 28, a gear 220 on the second deployment rod 194 engages a gear 222 on the actuator rod 218 so that when the actuator rod 218 is rotated in a first direction, and the first deployment rod 192 correspondingly rotates in that first direction, the second deployment rod 194 is rotated in the opposite direction.

FIG. 26 shows the apparatus 210 in a loading state in which the holding portions 212 of the deployment rods 192, 194 are positioned generally adjacent one another so that the harness 180 can be tightly wound thereupon like a scroll, as shown in FIG. 23. As the actuator rod 218 is rotated, the deployment arms 192, 194 move to an open position in which the holding portions 212 are spaced from each other, as shown in FIGS. 27 and 24. Continued rotation of the actuator continues the rotation of the deployment arms 192, 194, which eventually meet each other again as shown in FIG. 22. At this point the scroll harness has been deployed around the patient's heart 30 and needs only to be secured in place.

Sizing the Cardiac Harness

One consideration when applying a cardiac harness to a patient's heart in order to resist remodeling and promote reverse remodeling of the heart is to obtain a correctly sized cardiac harness to apply to the patient's heart. It is important to achieve a proper tension of the harness in order to apply an appropriate inwardly-directed compressive force so as to reduce wall stresses in the heart. If too much tension is provided, the heart could be constricted. If too little tension is provided, the device will provide reduced or no benefit for the patient.

Existing fabric harnesses, such as the Acorn™ Cardiac Support Device (CSD), require a surgeon to first loosely install the device over the patient's heart, and then manually tension the device while the device is in place. There is no algorithm or direction for the surgeon to determine and obtain the proper tension. This allows a potential for operator error and also allows for inconsistency between patients and surgeons.

Accordingly, it is desired to pre-size a cardiac harness to a patient's heart before installing the harness on the heart. Also, it is desired to have the pre-sizing procedure be as minimally invasive as possible for the patient.

Imaging data can be obtained non-invasively before any harness installation surgery is performed. Imaging such as echocardiography, CT Scanning, MRI Scanning, and ventriculography can be used. Other types of imaging can also be useful. It is anticipated that measuring the diameter of the heart, the volume of the heart, and the cross-sectional area of the heart at the end of diastole and at the end of systole will enable a clinician to determine a desired size of the heart and thus to design or prescribe a desired harness size and configuration.

Once a desired harness size and configuration is determined, the harness can be made from modular components in a manufacturer's or clinician's stock or can be custom fabricated for each patient. A particular harness size and/or configuration can be suitable for a range of heart sizes.

A harness can be chosen or made so that it applies a predetermined maximum epicardial pressure to the heart at the end of diastole. Preferably, the applied pressure at the end of diastole is greater than about 2 mm Hg but less than about 10 mm Hg, and more preferably is between about 4-8 mm Hg. Preferably, pressure is applied throughout the cardiac cycle and is greatest at the end of diastole.

In accordance with another embodiment, a cardiac harness is configured to be expandable beyond the end diastolic dimension to which it is sized in case the heart expands acutely. In this manner, pressure is applied to the epicardial surface at end diastole, but an end diastolic dimensional limit is not imposed on the heart.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A cardiac harness configured to fit about a patient's heart, comprising:
   a plurality of individual detached modules assembled together to form the harness by zip couplings having a coupling member for engaging zipper teeth.

2. The cardiac harness of claim 1, wherein the zipper teeth interlock.

3. The cardiac harness of claim 2, wherein the zipper teeth are attached to the harness.

4. The cardiac harness of claim 3, wherein the zipper teeth are mounted on fabric backing and attached to the harness with sutures.

5. The cardiac harness of claim 1, wherein the coupling member is configured to engage the zipper teeth in vivo.

6. The cardiac harness of claim 1, wherein the coupling member first engages the zipper teeth ex vivo and further engages the zipper teeth in vivo.

7. A cardiac harness configured to fit about a patient's heart, comprising:
   a plurality of individual modules assembled together to form the harness including a zip coupling having a coupling member for engaging zipper teeth, wherein at least one of the modules comprises a spring hinge.

8. The cardiac harness of claim 1, wherein the modules are configured for minimally invasive delivery.

9. The cardiac harness of claim 1, wherein the modules are configured for in vivo assembly.

10. A cardiac harness configured to fit about a patient's heart, comprising:
    a first module which extends along a first portion of a circumference of the harness; and
    a second module which extends along a second portion of the circumference of the harness;
    wherein the first and second modules are completely detached from one another until connected together by a zip coupling having a coupling member for engaging zipper teeth.

11. The cardiac harness of claim 10, wherein the first and second modules are connected to one another by the zipper teeth being interposed between the modules.

12. The cardiac harness of claim 10, wherein a secondary coupling is associated with the zipper teeth.

13. The cardiac harness of claim 10, wherein the first module and the second module are configured for minimally invasive delivery.

14. The cardiac harness of claim 13, wherein the first module and the second module are configured for in vivo assembly by using the coupling member to interlock the zipper teeth in vivo.

15. A method of making a cardiac harness, comprising:
    providing a plurality of detached modules; and
    connecting the detached modules to one another to form the harness by use of a zip coupling having a coupling member for interlocking zipper teeth.

16. The method of claim 15, wherein the zipper teeth are disposed between each module.

17. The method of claim 15, wherein the modules are assembled in vivo by using the coupling member to interlock the zipper teeth in vivo.

18. A method of making a cardiac harness, comprising:
    providing a plurality of modules; and
    connecting the modules to one another to form the harness by use of a zip coupling having a coupling member for interlocking zipper teeth, wherein the modules are assembled in vivo by using the coupling member to interlock the zipper teeth in vivo, wherein the modules are delivered to the heart by minimally invasive access prior to assembly in vivo.

19. A method of treating a diseased heart, comprising:
    providing a cardiac harness configured to fit about a patient's heart and comprising a first end and a second end, the first end and the second end being adapted to be coupled to one another;
    rolling at least a portion of the cardiac harness about an axis;
    placing the rolled cardiac harness adjacent a portion of the patient's heart;
    unrolling the harness so that the unrolled harness fits about the heart;
    coupling the first end and the second end using a zip coupling; and
    the zip coupling having a coupling member slidable along zipper teeth to interlock the zipper teeth.

20. The method of claim 19, wherein the coupling member is moved by hand to interlock the zipper teeth.

21. The method of claim 19, wherein the coupling member is moved by a tool to slidably interlock the zipper teeth.

22. The method of claim 19, wherein the coupling member slides along the zipper teeth to unzip and unlock the zipper teeth so that the harness can be repositioned on the heart.

23. The method of claim 19, wherein the cardiac harness is configured for minimally invasive delivery.

24. The cardiac harness of claim 1, wherein the coupling member engages the zipper teeth ex vivo.

25. The cardiac harness of claim 10, wherein the coupling member engages the zipper teeth ex vivo.

26. The method of claim 15, wherein the coupling member engages the zipper teeth ex vivo.

27. The method of claim 19, wherein the coupling member engages the zipper teeth ex vivo.

* * * * *

UNITED STATES PATENT AND TRADEMARK OFFICE
CERTIFICATE OF CORRECTION

PATENT NO.      : 7,435,213 B2
APPLICATION NO. : 10/754264
DATED           : October 14, 2008
INVENTOR(S)     : Lilip Lau et al.

It is certified that error appears in the above-identified patent and that said Letters Patent is hereby corrected as shown below:

Title Page, Inventors (75), after "Anuja Patel," delete "San Jose" and insert --Sunnyvale--.

Title Page, insert --Related U.S. Application Data
(63) Continuation of application No. 10/242,016, filed on Sep. 10, 2002, now Pat. No. 6,723,041.
(60) Provisional application No. 60/322,089, filed on Sep. 10, 2001.--.

Title Page, References Cited (56), delete "Pequignol" and insert --Pequignot--.

References Cited (56), Page 4, after "Coletta, C., et al., Prognostic Value of Left Ventricular Volume" delete "Responding" and insert --Response--.

References Cited (56), after "Capomolla, Soccorso, M.D., et al.., Dobutamine and Nitroprusside Infusion in Patients With Severe Congestive Heart Failure: Hemodynamic Improvement by" delete "Discordan" and insert --Discordant--.

Column 1, lines 5-7, after "This application" insert --is a continuation of U.S. patent application Ser. No. 10/242,016, filed Sep. 10, 2002, now U.S. Pat. No. 6,723,041, which--.

Signed and Sealed this

Tenth Day of February, 2009

JOHN DOLL
*Acting Director of the United States Patent and Trademark Office*